(12) United States Patent
Hilliard et al.

(10) Patent No.: US 9,333,288 B2
(45) Date of Patent: May 10, 2016

(54) ATTACHABLE PLUNGER ROD AND ASSOCIATED PACKAGING

(71) Applicant: Becton Dickinson France, S.A.S., Le Pont-de-Claix (FR)

(72) Inventors: Christopher Todd Hilliard, Bath, NC (US); Tracy Ray Hottovy, Columbus, NE (US); James Jude Pellegrini, Cary, NC (US)

(73) Assignee: Becton Dickinson France, S.A.S., Le Pont-de-Claix (FR)

( * ) Notice: Subject to any disclaimer, the term of this patent is extended or adjusted under 35 U.S.C. 154(b) by 551 days.

(21) Appl. No.: 13/622,391

(22) Filed: Sep. 19, 2012

(65) Prior Publication Data

US 2013/0081974 A1 Apr. 4, 2013

Related U.S. Application Data

(60) Provisional application No. 61/541,581, filed on Sep. 30, 2011.

(51) Int. Cl.
*B65D 81/26* (2006.01)
*B65D 69/00* (2006.01)
*A61M 5/00* (2006.01)
*A61M 5/315* (2006.01)

(52) U.S. Cl.
CPC ............. *A61M 5/002* (2013.01); *B65D 81/266* (2013.01); *A61M 2005/31518* (2013.01)

(58) Field of Classification Search
CPC .... B65D 51/244; B65D 51/30; B65D 81/266; A61M 5/002

USPC .......... 206/204, 205, 210, 363–366, 438, 57, 206/571, 38, 234; 604/181, 187, 232–236
See application file for complete search history.

(56) References Cited

U.S. PATENT DOCUMENTS

| | | | | |
|---|---|---|---|---|
| 1,581,341 | A | * 4/1926 | Guinness | ...................... 206/210 |
| 2,634,856 | A | 4/1953 | Perkins | |
| 2,720,969 | A | 10/1955 | Kendall | |
| 3,115,135 | A | 12/1963 | Sarnoff | |
| 3,545,607 | A | * 12/1970 | Keller | ........................... 206/365 |
| 3,746,155 | A | * 7/1973 | Seeley | .......................... 206/365 |
| 3,869,062 | A | 3/1975 | Jaeschke et al. | |
| 4,011,868 | A | 3/1977 | Friend | |
| 4,184,593 | A | * 1/1980 | Dorr | ............................. 206/365 |
| 4,421,235 | A | 12/1983 | Moriya | |

(Continued)

FOREIGN PATENT DOCUMENTS

| | | |
|---|---|---|
| GB | 2233564 A | 1/1991 |
| JP | 8173533 A | 7/1996 |

(Continued)

*Primary Examiner* — Luan K Bui
(74) *Attorney, Agent, or Firm* — The Webb Law Firm

(57) ABSTRACT

A syringe assembly including a plunger rod separate and detached from a syringe barrel and a packaging member, the plunger rod having a sealing member and the packaging member having a first compartment and a second compartment is disclosed. With the syringe barrel received within the first compartment and the plunger rod received within the second compartment, the sealing member of the plunger rod seals the syringe barrel and the plunger rod within the packaging member. In this manner, the syringe assembly is placed in the packaging member in a manner that allows for reduced storage space of the syringe assembly.

9 Claims, 27 Drawing Sheets

(56) References Cited

U.S. PATENT DOCUMENTS

| | | | |
|---|---|---|---|
| 4,497,406 A | 2/1985 | Takanashi | |
| 4,501,360 A * | 2/1985 | Levy | 206/443 |
| 4,537,305 A | 8/1985 | Takanashi | |
| 4,551,135 A | 11/1985 | Gorman et al. | |
| 4,581,023 A * | 4/1986 | Kuntz | 604/234 |
| 4,615,468 A | 10/1986 | Gay | |
| D287,806 S * | 1/1987 | Borin | D7/317 |
| 4,820,306 A | 4/1989 | Gorman et al. | |
| 4,872,553 A | 10/1989 | Suzuki et al. | |
| 4,936,314 A | 6/1990 | Kasai et al. | |
| 5,769,825 A | 6/1998 | Lynn | |
| 5,775,498 A * | 7/1998 | Kashanchi | 206/364 |
| 5,928,560 A | 7/1999 | DelDuca et al. | |
| 5,947,935 A | 9/1999 | Rhinehart et al. | |
| 6,007,529 A | 12/1999 | Gustafsson et al. | |
| 6,017,330 A | 1/2000 | Hitchins et al. | |
| 6,059,756 A | 5/2000 | Yeh | |
| 6,063,503 A | 5/2000 | Hatakeyama et al. | |
| 6,503,587 B2 | 1/2003 | Kashiba et al. | |
| 6,508,955 B1 | 1/2003 | DelDuca et al. | |
| 6,559,205 B2 | 5/2003 | Cai et al. | |
| 6,682,791 B2 | 1/2004 | McKnight | |
| 6,746,772 B2 | 6/2004 | Kashiba et al. | |
| 7,056,301 B2 | 6/2006 | Liu | |
| 7,056,565 B1 | 6/2006 | Cai et al. | |
| 7,494,605 B2 | 2/2009 | Dayrit et al. | |
| 7,708,719 B2 | 5/2010 | Wilmot et al. | |
| 8,029,842 B2 | 10/2011 | Powers | |
| 8,048,201 B2 | 11/2011 | Dukes et al. | |
| 2003/0106824 A1 * | 6/2003 | Wilmot et al. | 206/439 |
| 2005/0072958 A1 | 4/2005 | Powers | |
| 2007/0078402 A1 | 4/2007 | Yang | |
| 2008/0072992 A1 | 3/2008 | Baleriaux et al. | |
| 2008/0255523 A1 * | 10/2008 | Grinberg | 604/192 |
| 2008/0300551 A1 | 12/2008 | Schiller et al. | |
| 2009/0157008 A1 | 6/2009 | Vitral | |
| 2010/0152673 A1 | 6/2010 | Fang | |
| 2010/0174268 A1 | 7/2010 | Wilmot et al. | |
| 2010/0282633 A1 | 11/2010 | Chau et al. | |
| 2011/0009830 A1 | 1/2011 | Kosinski et al. | |
| 2011/0079525 A1 | 4/2011 | Peck et al. | |
| 2011/0155621 A1 | 6/2011 | Lindquist et al. | |
| 2011/0217430 A1 | 9/2011 | Chau et al. | |
| 2011/0264052 A1 | 10/2011 | Oliver | |
| 2011/0272310 A1 | 11/2011 | Tennican | |
| 2012/0143144 A1 | 6/2012 | Young | |

FOREIGN PATENT DOCUMENTS

| | | |
|---|---|---|
| JP | 8243161 A | 9/1996 |
| JP | 2003292055 A | 10/2003 |
| JP | 2008067989 A | 3/2008 |
| JP | 2009154925 A | 7/2009 |
| WO | 9922691 A1 | 5/1999 |
| WO | 2009150043 A1 | 12/2009 |
| WO | 2011004137 A1 | 1/2011 |

* cited by examiner

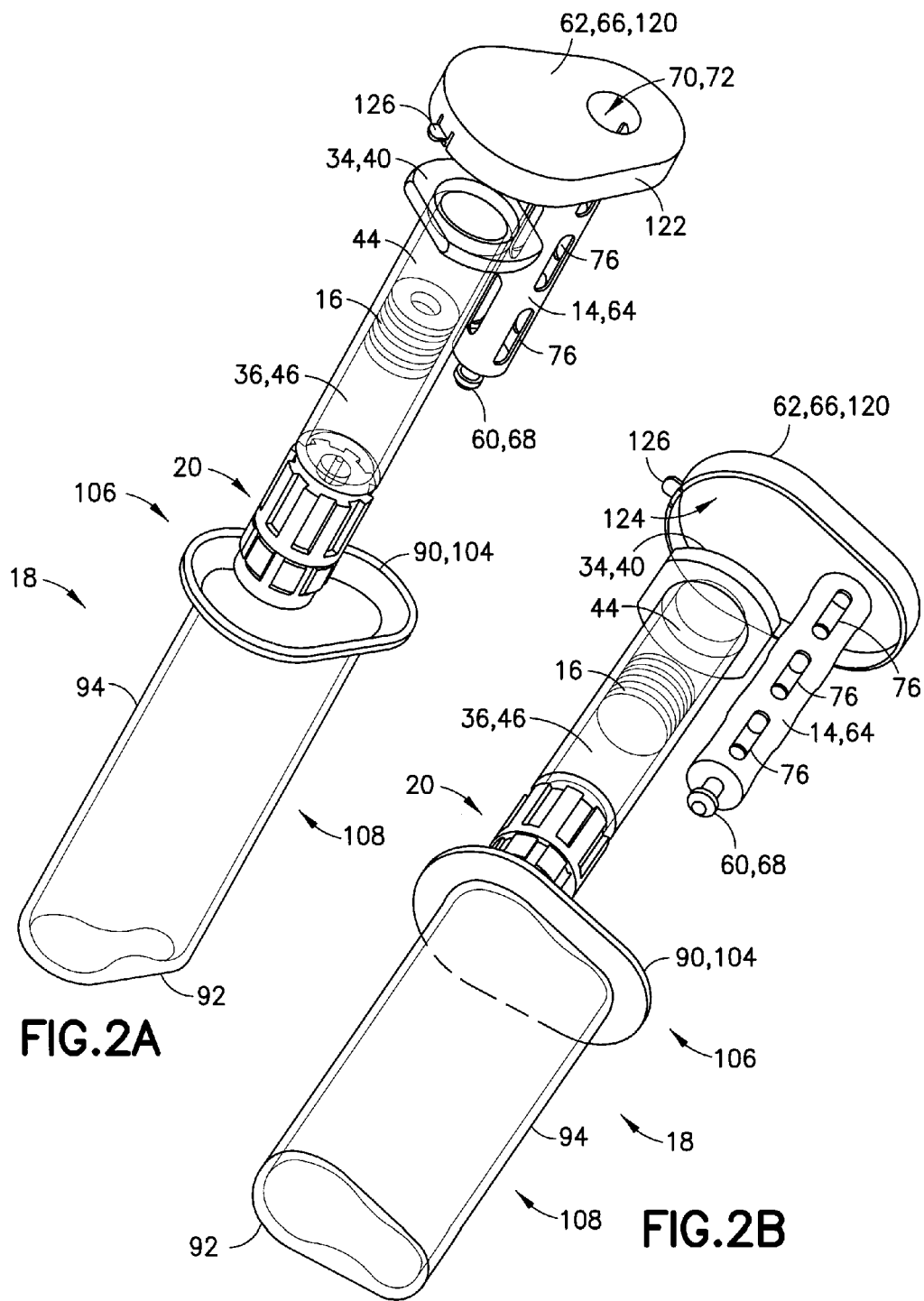

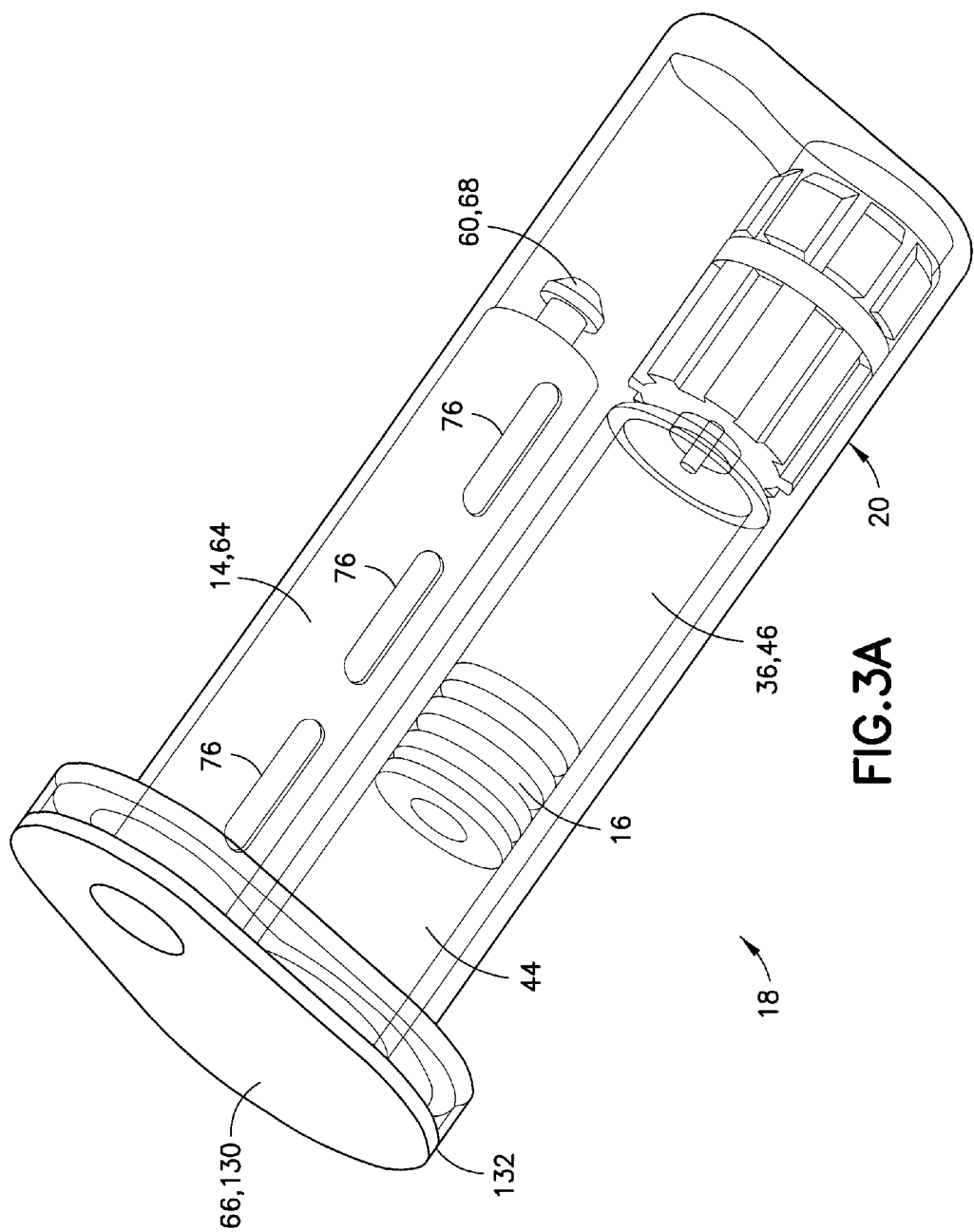

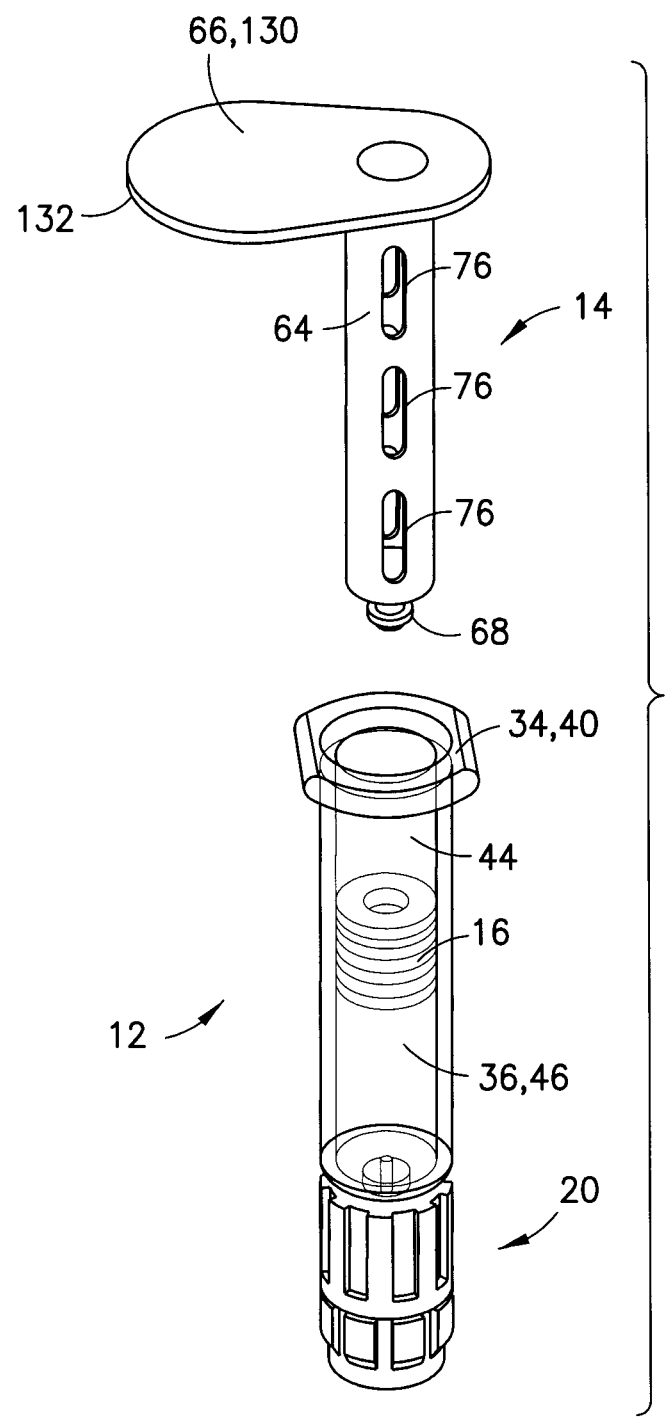

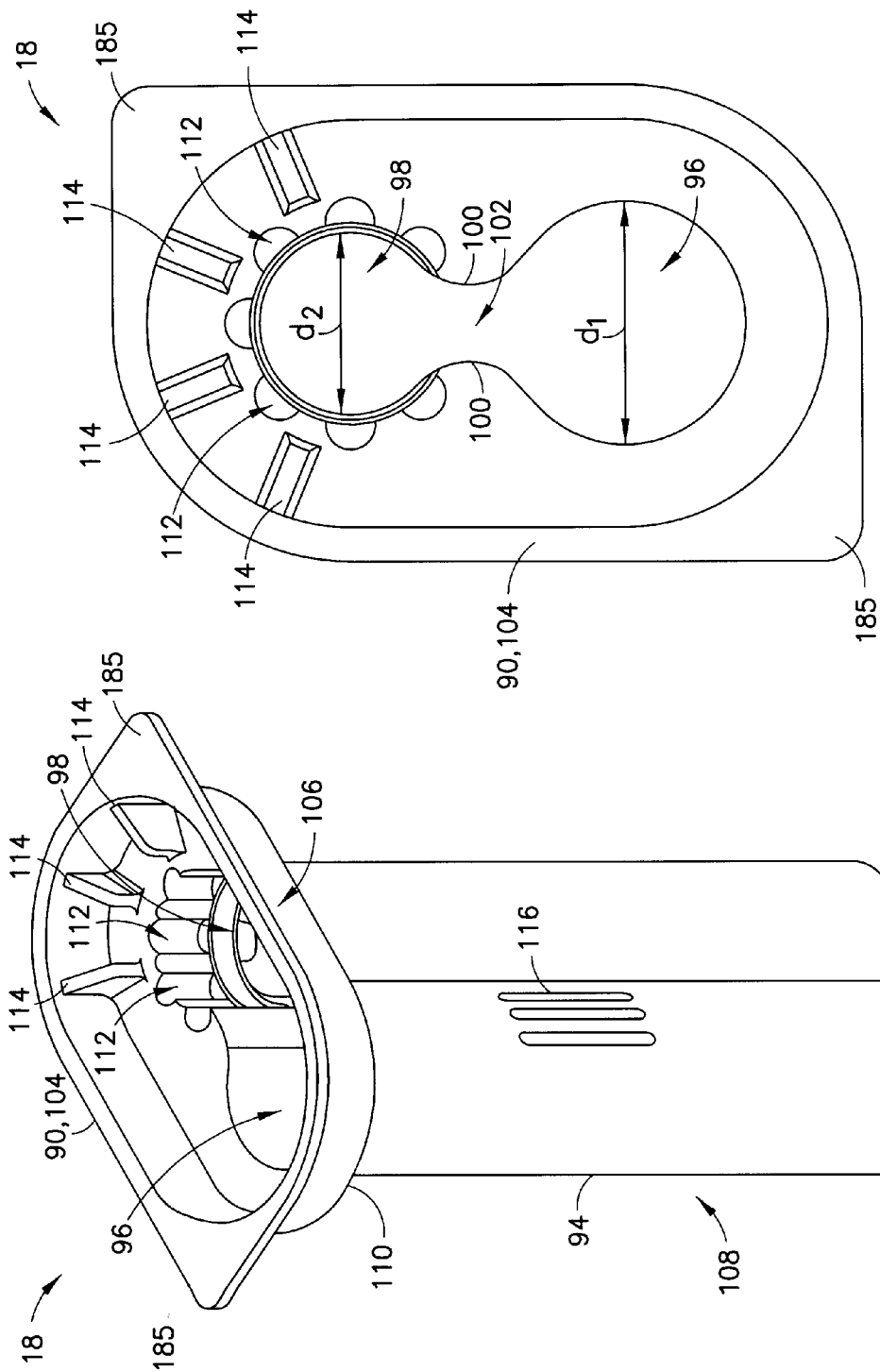

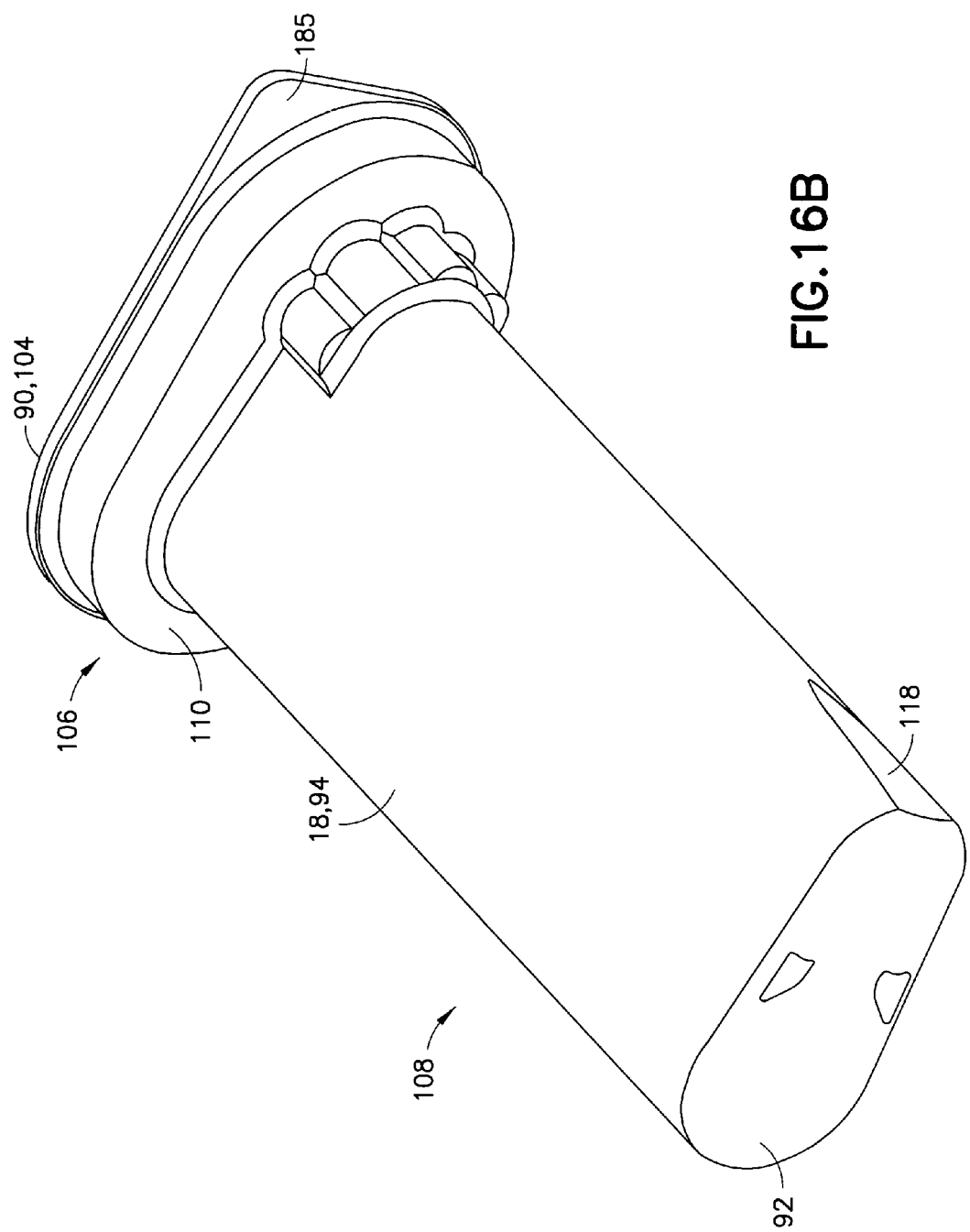

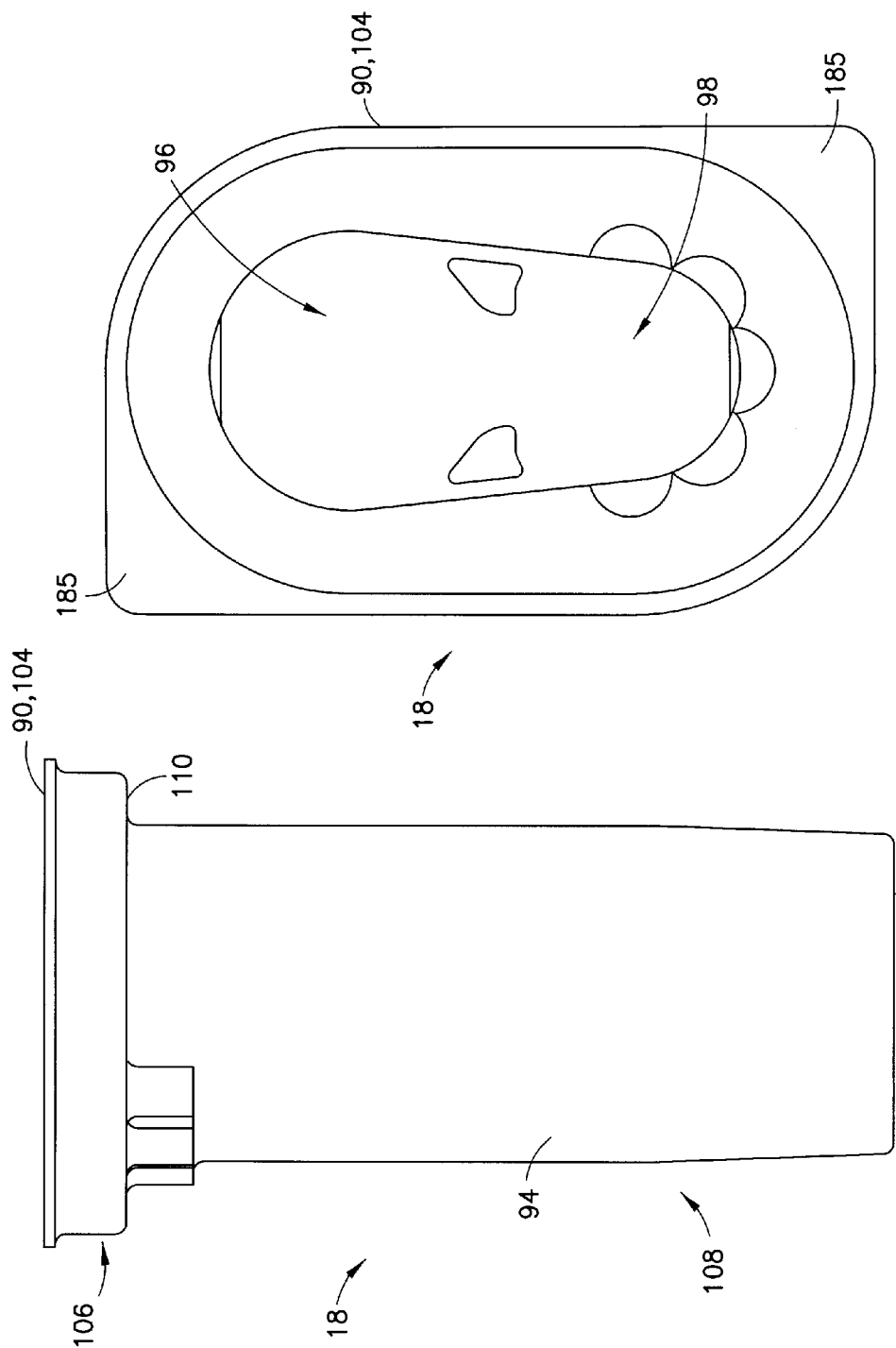

ATTACHABLE PLUNGER ROD AND ASSOCIATED PACKAGING

CROSS-REFERENCE TO RELATED APPLICATION

This application claims priority to U.S. Provisional Application Ser. No. 61/541,581 filed Sep. 30, 2011, the entire disclosure of which is hereby incorporated by reference.

BACKGROUND OF THE INVENTION

1. Field of the Disclosure

The present disclosure relates generally to a syringe assembly adapted for delivery of a fluid and/or collection of a fluid. More particularly, the present disclosure relates to a syringe assembly in which the plunger rod and the syringe barrel may be placed in a packaging member in a manner that allows for reduced storage space of the syringe assembly.

2. Description of the Related Art

Syringe assemblies, and in particular hypodermic syringes, are well known in the medical field for dispensing fluids, such as medications. A conventional syringe typically includes a syringe barrel with an opening at one end and a plunger mechanism disposed through the opposite end. The plunger mechanism typically includes a plunger rod extending through the barrel, with a plunger head or stopper disposed at the end of the plunger rod within the syringe barrel, and with a finger flange at the other end of the plunger rod extending out of the syringe barrel. In use, the plunger rod is retracted through the syringe barrel to aspirate or fill the syringe barrel with a fluid, such as a medication, with the plunger rod extending out from the rear end of the syringe barrel. For delivery of the medication to a patient, the opening of the syringe barrel is adapted for fluid communication with a patient, such as through a hypodermic needle fitted at the front end of the syringe barrel or through a luer-type fitting extending from the syringe barrel for attachment with a fluid line of a patient. Upon the user applying a force to depress the plunger rod and stopper through the syringe barrel towards the front end of the syringe barrel, the contents of the syringe are thereby forced out of the syringe barrel through the opening at the front end for delivery to the patient. Such an operation is well known in the medical field, and medical practitioners have become well accustomed to the use of such common fluid delivery procedures through standard syringes.

Conventional syringes are well known in the medical field to be used in connection with a vial of a medication, where the user collects or draws the fluid into the syringe immediately prior to injection and delivery of the fluid to the patient. Commonly, hypodermic syringes may be packaged as "pre-filled" devices, wherein the syringe is pre-filled with medication prior to being packaged and delivered to the patient. In this manner, the need for the user to fill the device prior to injection is eliminated, thereby saving time and maintaining consistent volumes for delivery.

However, packaging of such pre-filled syringes tends to be bulky and difficult to ship and store. A pre-filled syringe is typically packaged with the opening at the front end of the barrel including a cap thereover and with the plunger rod retracted out of the back end of the syringe barrel, with the fluid pre-filled within the syringe barrel. Such packaging creates an elongated package that can be awkward for shipping and storage.

Pre-filled syringes and pre-filled metered dose syringes are often filled with fluids, such as a medication, at a production facility, packaged, and then shipped to a medical facility. Once at the facility, these syringes are often placed in controlled storage and/or locked cabinets to reduce theft of the syringes themselves and/or of the contents of these syringes. The space within these controlled storage locations is often limited, thus there is a need for a syringe assembly that has a smaller packaging footprint to reduce the amount of storage space required for containing the syringe.

SUMMARY OF THE INVENTION

In accordance with an embodiment of the present invention, a syringe assembly is provided which, in one embodiment, includes a plunger rod separate and detached from a syringe barrel and a packaging member, the plunger rod having a sealing member and the packaging member having a first compartment and a second compartment. With the syringe barrel received within the first compartment and the plunger rod received within the second compartment, the sealing member of the plunger rod seals the syringe barrel and the plunger rod within the packaging member. The syringe assembly of the present disclosure is placed in the packaging member in a manner that allows for reduced storage space of the syringe assembly. In one embodiment, the syringe assembly of the present disclosure includes a securement feature or engagement portion connected to the plunger rod and a stopper slidably disposed within the interior of the syringe barrel, the engagement portion operable to secure the plunger rod to the stopper. In this manner, upon removal of the plunger rod and the syringe barrel from the packaging member, the plunger rod can quickly and easily be secured to the syringe barrel via the stopper for collecting a fluid and/or delivering a fluid.

The present disclosure, in one embodiment thereof, includes a syringe packaging system including a syringe barrel having a first end, a second end, and a sidewall extending therebetween and defining a chamber having an interior, and a stopper slidably disposed within the interior of the syringe barrel. The syringe packaging system of this embodiment includes a plunger rod having a first end engageable with a portion of the stopper, a second end, and a sealing member disposed adjacent the second end. The syringe packaging system further includes a packaging member having a first end, a second end, and a sidewall defining a first compartment and a second compartment each extending between the first end and the second end of the packaging member, the first compartment sized and adapted to receive the syringe barrel therein, and the second compartment sized and adapted to receive the plunger rod therein, wherein with the syringe barrel received within the first compartment of the packaging member and the plunger rod received within the second compartment of the packaging member, the sealing member of the plunger rod seals the syringe barrel and the plunger rod within the packaging member. Optionally, the packaging member is substantially rigid.

The present disclosure, in another embodiment thereof, includes a syringe assembly including a syringe barrel having a first end, a second end, and a sidewall extending therebetween and defining a chamber having an interior, and a stopper slidably disposed within the interior of the syringe barrel and defining an aperture therein, the stopper comprising a deformable restraining member adjacent the aperture, the deformable restraining member transitionable between a deformed position to an undeformed position. The syringe assembly of this embodiment includes a plunger rod having a first end, a second end, and a plunger rod head disposed adjacent the first end of the plunger rod, wherein as the plunger rod head is moved axially within the aperture of the stopper, the plunger rod head deforms the restraining member of the stopper, and once the plunger rod head is advanced beyond the restraining member of the stopper, the restraining member returns to its undeformed position to secure the plunger rod head within the aperture.

The present disclosure, in a further embodiment thereof, includes a syringe assembly including a syringe barrel having a first end, a second end, and a sidewall extending therebetween and defiling a chamber having an interior, and a stopper slidably disposed within the interior of the chamber of the syringe barrel and defining an aperture therein, the stopper comprising a protruding member adjacent the aperture. The syringe assembly of this embodiment includes a plunger rod having a first end, a second end, and a plunger rod head disposed adjacent the first end of the plunger rod, the plunger rod head comprising a deformable restraining member transitionable between a deformed position to an undeformed position, wherein as the plunger rod head is moved axially within the aperture of the stopper, the protruding member of the stopper deforms the restraining member of the plunger rod head, and once the plunger rod head is advanced beyond the protruding member of the stopper, the restraining member returns to its undeformed position to secure the plunger rod head within the aperture.

The present disclosure, in another embodiment thereof, includes a syringe packaging system including a syringe barrel having a first end, a second end, and a sidewall extending therebetween and defining a chamber having an interior, and a stopper slidably disposed within the interior of the syringe barrel. The syringe packaging system of this embodiment includes a plunger rod having a first end engageable with a portion of the stopper and a second end, and an oxygen absorber contained within the plunger rod. The syringe packaging system further includes a packaging member having a first end, a second end, and a sidewall defining a first compartment and a second compartment each extending between the first end and the second end of the packaging member, the first compartment sized and adapted to receive the syringe barrel therein and the second compartment sized and adapted to receive the plunger rod therein. Optionally, the packaging member is substantially rigid.

BRIEF DESCRIPTION OF THE DRAWINGS

FIG. 2A is a perspective view of a syringe assembly in accordance with an embodiment of the present invention.

FIG. 2B is a perspective view of the syringe assembly of FIG. 2A in accordance with an embodiment of the present invention.

FIG. 3A is a perspective view of the syringe assembly of FIG. 1, with a syringe barrel and a plunger rod placed in a packaging member, and a sealing member of the plunger rod sealing the syringe barrel and the plunger rod within the packaging member in accordance with an embodiment of the present invention.

FIG. 4 is an exploded, perspective view of the syringe barrel and the plunger rod of FIG. 1 in accordance with an embodiment of the present invention.

FIG. 8A is a perspective view of a packaging member in accordance with an embodiment of the present invention.

FIG. 8B is a plan view of the packaging member of FIG. 8A in accordance with an embodiment of the present invention.

FIG. 16B is a perspective view of the packaging member of FIG. 16A in accordance with an embodiment of the present invention.

FIG. 16C is a side elevation view of the packaging member of FIG. 16A in accordance with an embodiment of the present invention.

FIG. 16D is a plan view of the packaging member of FIG. 16A in accordance with an embodiment of the present invention.

DETAILED DESCRIPTION

Figure 1:
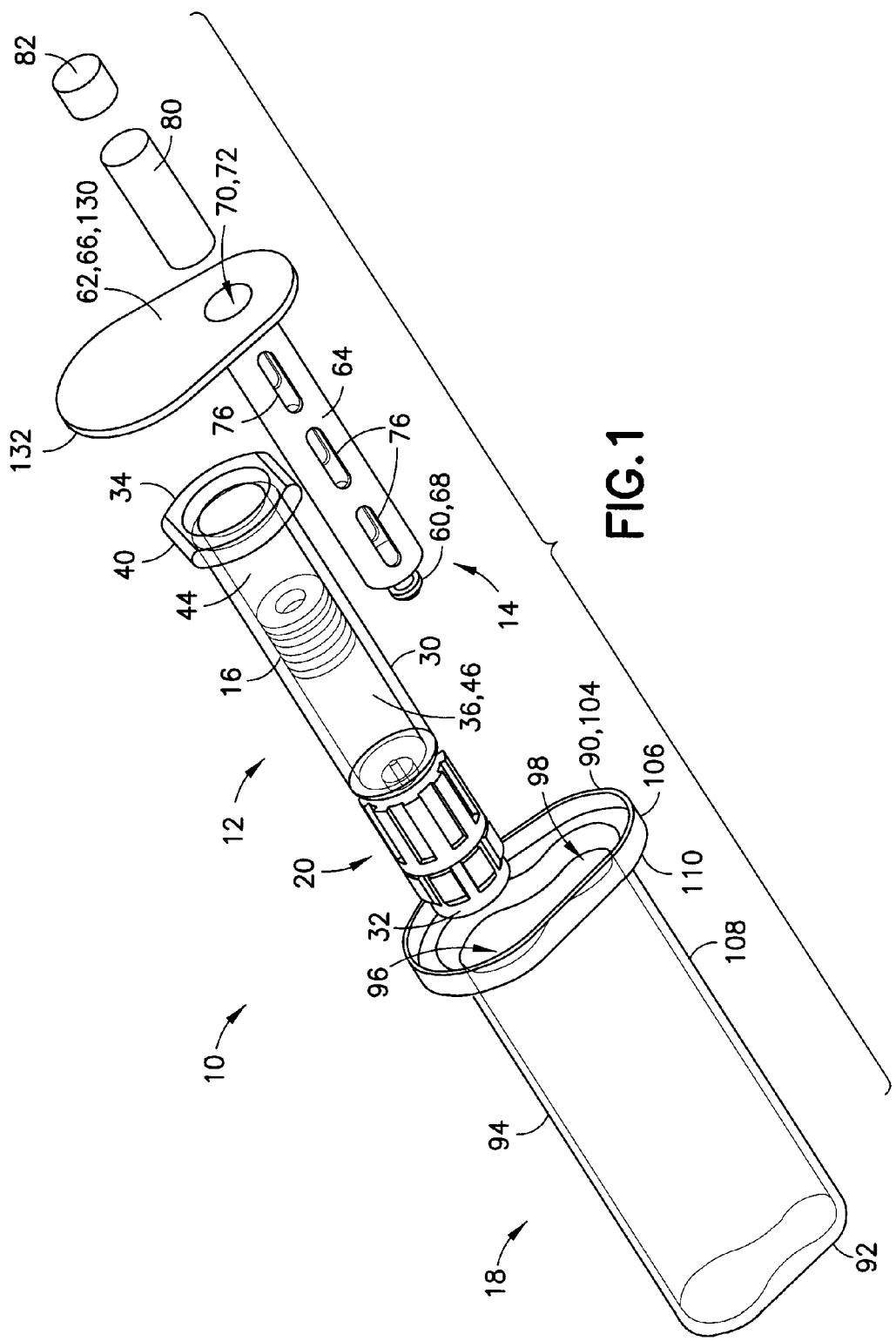
FIG. 1 is an exploded, perspective view of a syringe assembly in accordance with an embodiment of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

In the following discussion, "distal" refers to a direction generally toward an end of a syringe assembly adapted for contact with a patient and/or engagement with a separate device such as a needle assembly or IV connection assembly, and "proximal" refers to the opposite direction of distal, i.e., away from the end of a syringe assembly adapted for engagement with the separate device. For purposes of this disclosure, the above-mentioned references are used in the description of the components of a syringe assembly in accordance with the present disclosure.

Figure 6A:
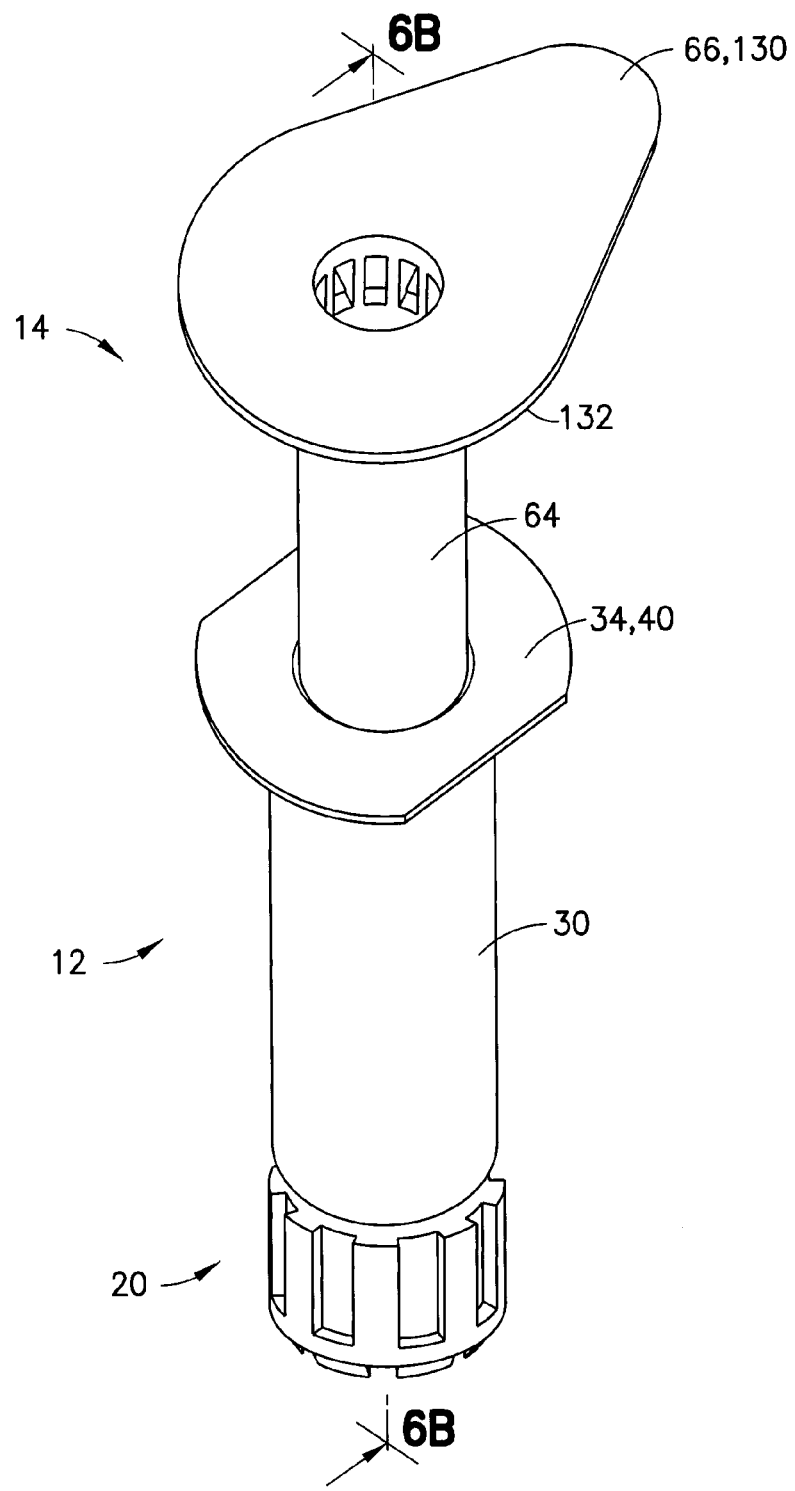
FIG. 6A is an assembled, perspective view of the syringe barrel and the plunger rod of FIG. 4, illustrating an alternative embodiment of a flange of the plunger rod and the syringe barrel in accordance with an embodiment of the present invention.
Figure 6B:
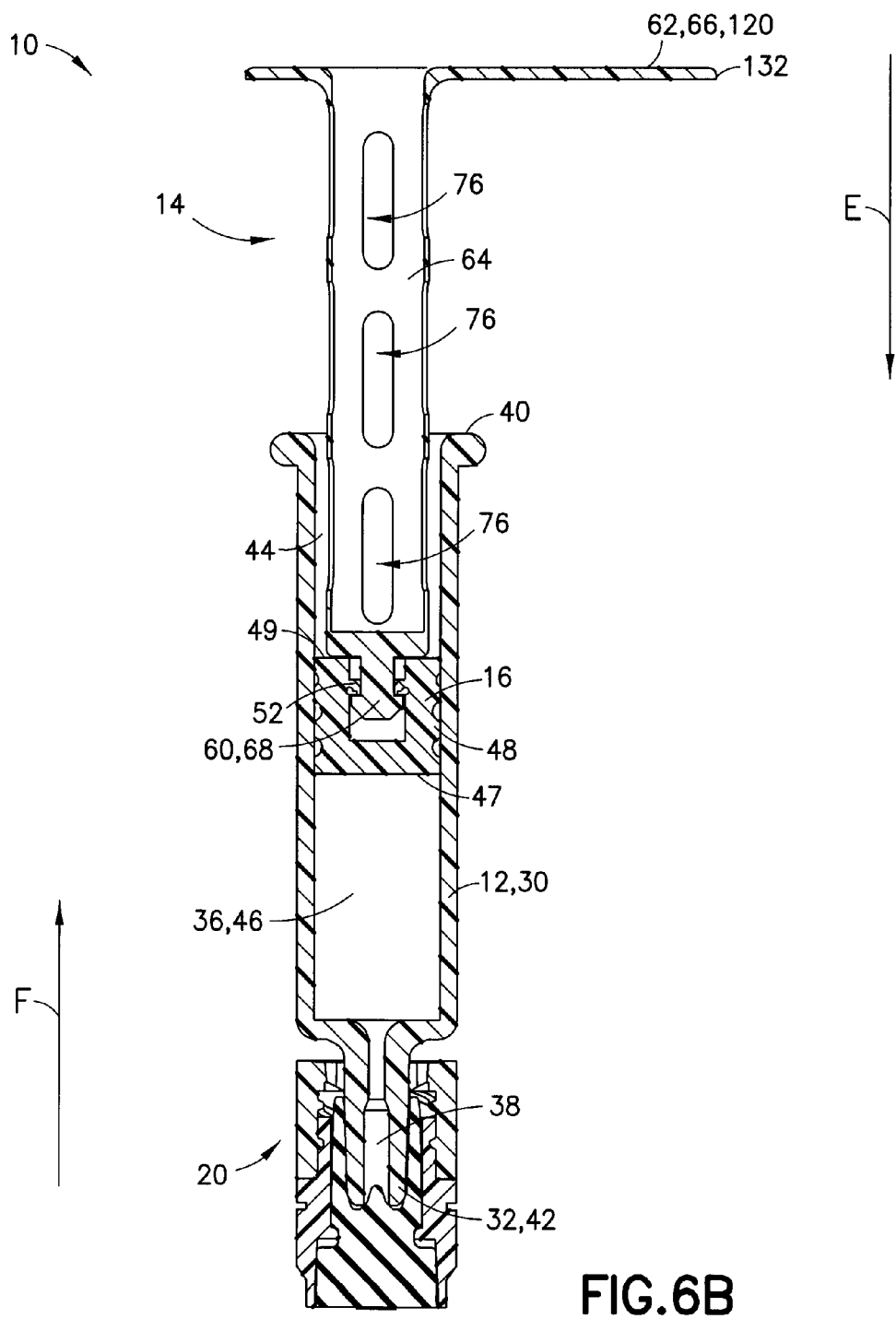
FIG. 6B is a cross-sectional view taken along line 6B-6B of FIG. 6A in accordance with an embodiment of the present invention.
Figure 7:
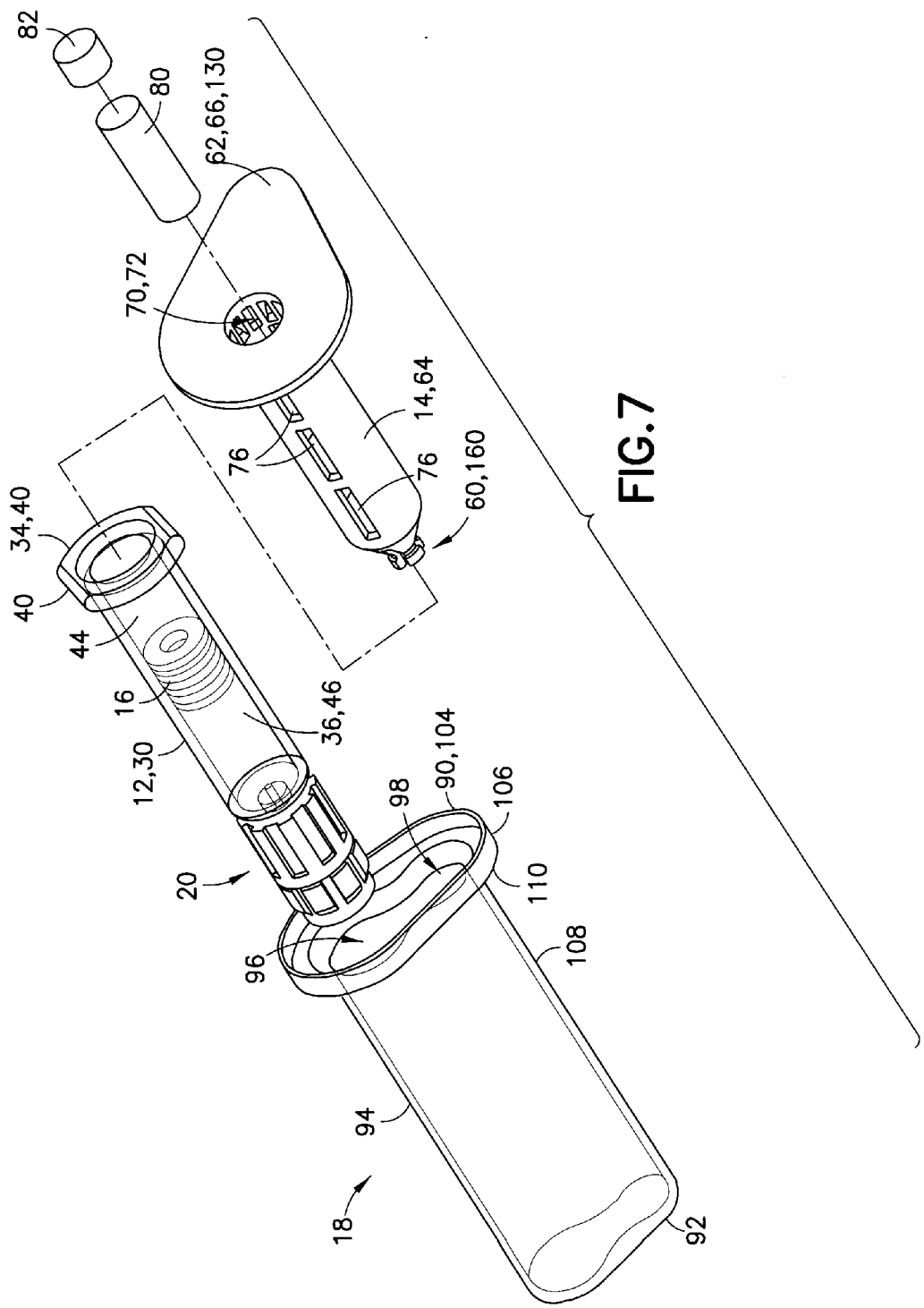
FIG. 7 is an exploded, perspective view of a syringe assembly in accordance with an embodiment of the present invention.

Referring to FIGS. 1 and 6B, a syringe assembly 10 includes a syringe barrel 12, a separate or detached plunger rod 14, a stopper 16, and a packaging member 18. Syringe assembly 10 may be adapted for dispensing and delivery of a fluid and/or collection of a fluid. For example, syringe assembly 10 may be used for injection or infusion of fluid such as a medication into a patient. Syringe assembly 10 is contemplated for use in connection with a needle, such as by connecting syringe assembly 10 to a separate needle assembly (not shown), or alternatively for connection with an intravenous (IV) connection assembly (not shown). It can be appreciated that the present disclosure can be used with any type of syringe assembly, particularly those which are placed in a controlled storage environment in which storage space is limited. These types of syringes include traditional pre-filled syringe assemblies, metered dose syringes, aspiration syringes for withdrawing fluid from a patient or medication from a container, and the like.

Referring to FIGS. 1, 3C, 4, and 6B, syringe barrel 12 generally includes a barrel body or sidewall 30 extending between a first or distal end 32 and a second or proximal end 34. Sidewall 30 defines an elongate aperture or interior chamber 36 of syringe barrel 12. In one embodiment, interior chamber 36 may span the extent of syringe barrel 12 so that syringe barrel 12 is cannulated along its entire length. In one embodiment, syringe barrel 12 may be in the general form of an elongated cylindrical barrel as is known in the art in the general shape of a hypodermic syringe. In alternative embodiments, syringe barrel 12 may be in other forms for containing a fluid for delivery, such as in the general form of an elongated rectangular barrel, for example. Syringe barrel 12 may be formed of glass, or may be injection molded from thermoplastic material such as polypropylene and polyethylene according to techniques known to those of ordinary skill in the art, though it is to be appreciated that syringe barrel 12 may be made from other suitable materials and according to other applicable techniques. In certain configurations, syringe barrel 12 may include an outwardly extending flange 40 about at least a portion of proximal end 34. Flange 40 may be configured for easy grasping by a medical practitioner, as will be discussed herein.

Distal end 32 of syringe barrel 12 includes an outlet opening 38 (FIGS. 3C and 6B) which is in fluid communication with chamber 36. Outlet opening 38 may be sized and adapted for engagement with a separate device, such as a needle assembly or IV connection assembly and, therefore, may include a mechanism for such engagement as is conventionally known. For example, distal end 32 may include a generally-tapered luer tip 42 (FIGS. 3C and 6B) for engagement with an optional separate tapered luer structure of such a separate device for attachment therewith (not shown). In one configuration, both the tapered luer tip 42 and the separate tapered luer structure may be provided with syringe assembly 10. In such a configuration, the separate tapered luer structure may be fitted with an attachment mechanism, such as a threaded engagement, for corresponding engagement with a separate device (not shown). In another configuration, tapered luer tip 42 may be provided for direct engagement with a separate device (not shown). In addition, a mechanism for locking engagement therebetween may also be provided with at least one of tapered luer tip 42 and/or the separate tapered luer structure, such as a luer collar or luer lock including interior threads. Such luer connections and luer locking mechanisms are well known in the art.

Proximal end 34 of syringe barrel 12 is generally open-ended, but is intended to be closed off to the external environment as discussed herein. Syringe barrel 12 may also include markings, such as graduations located on sidewall 30, for providing an indication as to the level or amount of fluid contained within interior chamber 36 of syringe barrel 12. Such markings may be provided on an external surface of sidewall 30, an internal surface of sidewall 30, or integrally formed or otherwise within sidewall 30 of syringe barrel 12. In other embodiments, alternatively, or in addition thereto, the markings may also provide a description of the contents of the syringe or other identifying information as may be known in the art, such as maximum and/or minimum fill lines.

Syringe assembly 10 may be useful as a pre-filled syringe, and, therefore, may be provided for end use with a fluid, such as a medication or drug, contained within interior chamber 36 of syringe barrel 12, pre-filled by the manufacturer. In this manner, syringe assembly 10 can be manufactured, pre-filled with a medication, sterilized, and packaged in appropriate packaging such as packaging member 18 for delivery, storage, and use by the end user, without the need for the end user to fill the syringe with medication from a separate vial prior to use. In such an embodiment, syringe assembly 10 may include sealing cap member 20 disposed at distal end 32 of syringe barrel 12 to seal a fluid, such as a medication, within interior chamber 36 of syringe barrel 12 as described above.

Referring to FIGS. 1, 2A, 2B, 4, and 6B, syringe assembly 10 includes stopper 16 which is moveably or slidably disposed within interior chamber 36, and in sealing contact with the internal surface of sidewall 30 of syringe barrel 12, thereby separating interior chamber 36 into a proximal chamber 44 adjacent proximal end 34, and a distal chamber 46 adjacent distal end 32. Stopper 16 is sized relative to syringe barrel 12 to provide sealing engagement with the interior surface of sidewall 30 of syringe barrel 12. Additionally, stopper 16 may include one or more annular ribs 48 (FIGS. 3C, 5A, 5B, and 6B) extending around the periphery of stopper 16 to increase the sealing engagement between stopper 16 and the interior surface of sidewall 30 of syringe barrel 12. In alternate embodiments, a singular O-ring or a plurality of O-rings may be circumferentially disposed about stopper 16 to increase the sealing engagement with the interior surface of sidewall 30.

Figure 5A:
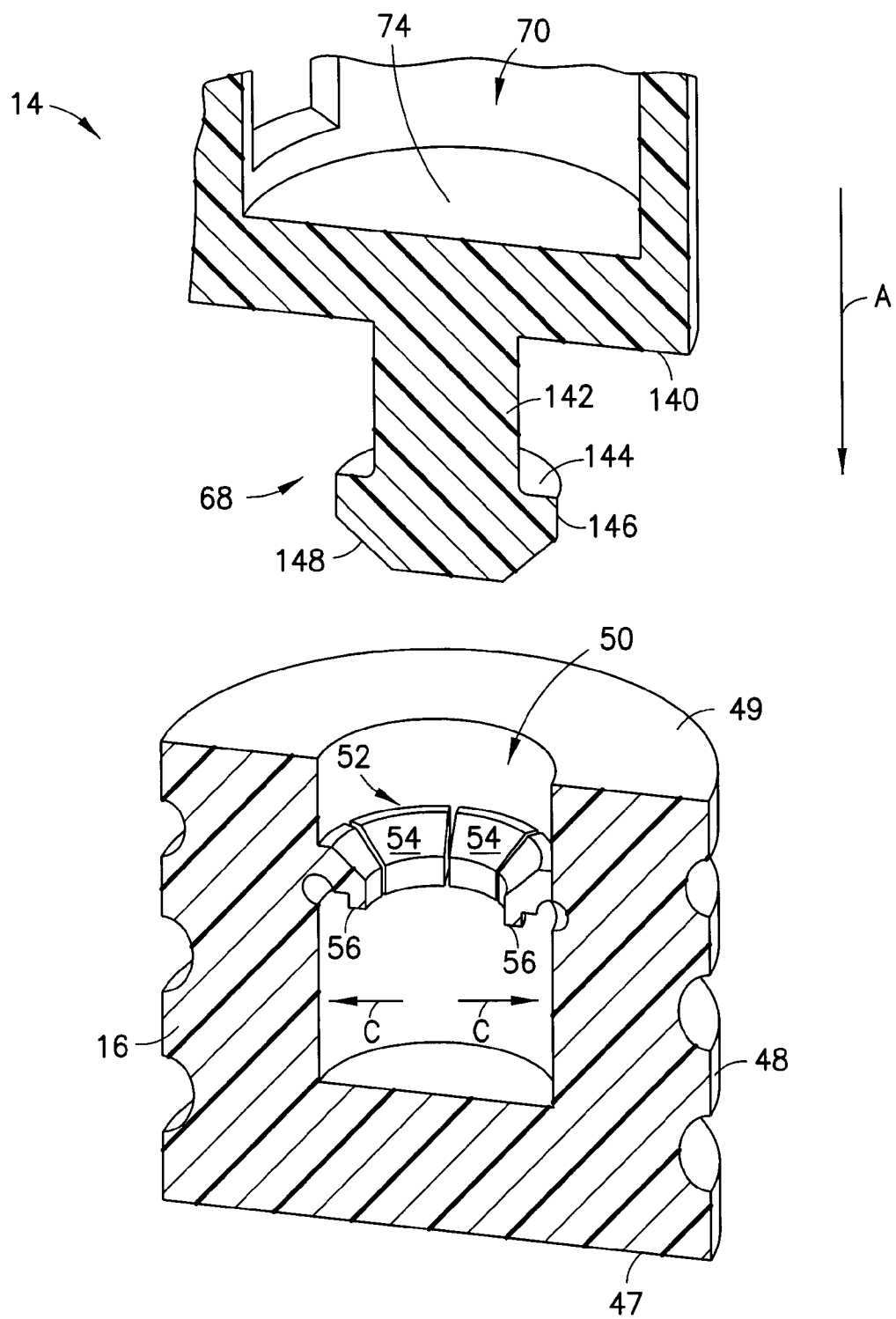
FIG. 5A is a fragmentary, cross-sectional view of a securement feature of the syringe barrel and the plunger rod of FIG. 4 in a disengaged position in accordance with an embodiment of the present invention.
Figure 5B:
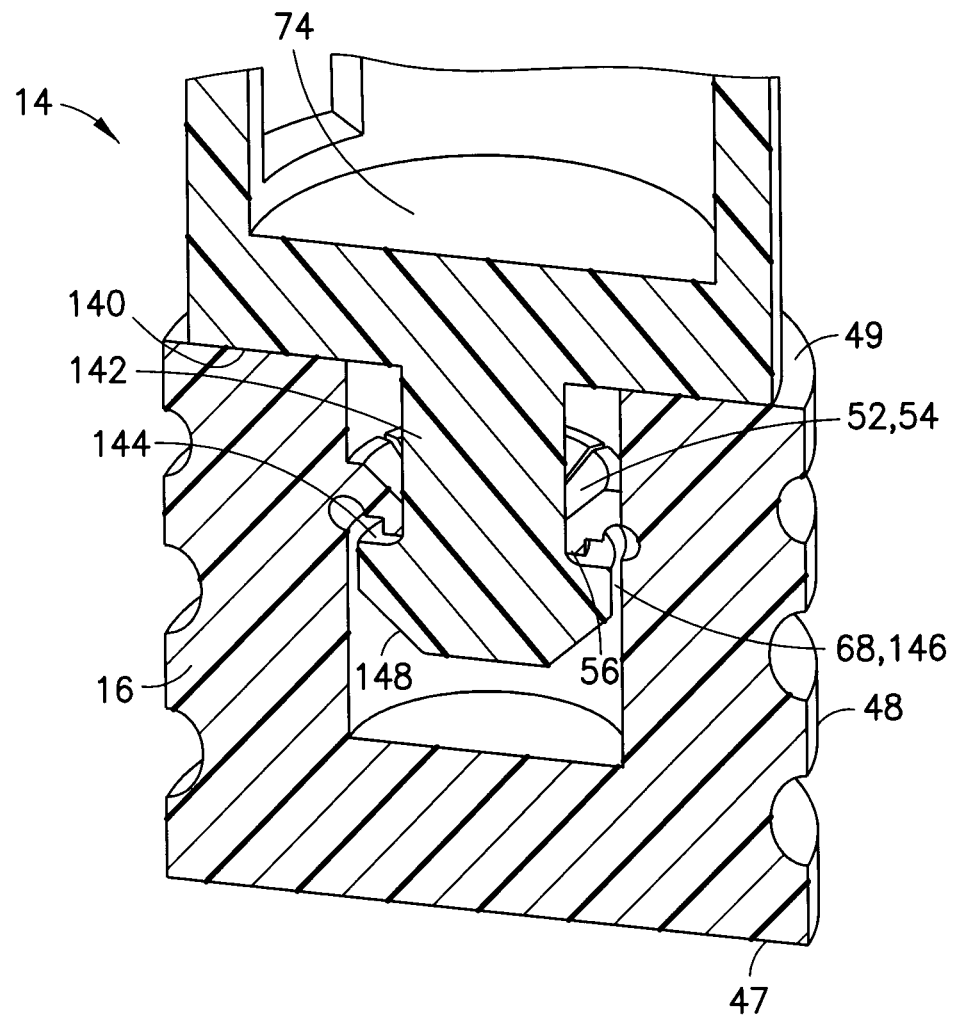
FIG. 5B is a fragmentary, cross-sectional view of a securement feature of the syringe barrel and the plunger rod of FIG. 4 in an engaged position in accordance with an embodiment of the present invention.

Referring to FIGS. 5A, 5B, and 6B, in one embodiment, stopper 16 also includes a first or distal end 47 and a second or proximal end 49 defining a plunger receiving aperture 50 formed therein and having a securement feature or engagement portion such as a deformable restraining member for securing plunger rod 14 to stopper 16. In one embodiment, referring to FIGS. 5A and 5B, the engagement portion or deformable restraining member of stopper 16 may include elastic fingers 52 extending into aperture 50 for securing plunger rod 14 to stopper 16 as will be described in more detail below. The deformable restraining member is transitionable between a deformed position to an undeformed position as described in more detail below. In one embodiment, the deformable restraining member includes at least one deformable finger. Each elastic finger 52 of stopper 16 generally includes a tapered portion 54 and a locking end 56. In other embodiments, the engagement portion of stopper 16 may include a threaded portion, snap fit mechanism, a ball detent, locking tabs, spring loaded locking mechanism, latch, adhesive, or other similar mechanism. In another alternative embodiment, referring to FIGS. 15A and 15B, the engagement portion of stopper 16 may include a protruding member 150 having a tapered portion 152, a locking end 154, and a protrusion 156 disposed between tapered portion 152 and locking end 154 as will be described in more detail below. In one embodiment, protruding member 150 is formed of a rigid, unyielding material.

Referring to FIGS. 1, 2A, 2B, 4, 6A, and 6B, syringe assembly 10 further includes plunger rod 14 which provides a mechanism for dispensing fluid contained within interior chamber 36 of syringe barrel 12 through outlet opening 38 upon connection of plunger rod 14 to syringe barrel 12 via stopper 16 as will be described in more detail below. Plunger rod 14 is adapted for advancing stopper 16. In one embodiment, plunger rod 14 is sized for movement within interior chamber 36 of syringe barrel 12 as will be discussed in more detail below, and generally includes a first or distal end 60, a second or proximal end 62, a plunger rod body 64 extending between first end 60 and second end 62, a sealing member or flange 66 disposed adjacent second end 62, and a securement feature or engagement portion for securing plunger rod 14 to stopper 16. In one embodiment, the engagement portion of plunger rod 14 may include a plunger rod head 68 disposed adjacent first end 60 for securing plunger rod 14 to stopper 16 as will be described in more detail below. In one embodiment, referring to FIGS. 5A and 5B, plunger rod head 68 may include a stopper contacting portion 140 and a neck 142 extending between stopper contacting portion 140 and plunger rod head 68. Plunger rod head 68 has a cross-section that has a greater area than a cross-section disposed below plunger rod head 68, i.e., neck 142, such that a shoulder wall 144 is defined therebetween. Plunger rod head 68 also includes a sidewall 146 and a tapered portion 148. In one embodiment, plunger rod head 68 is formed of a rigid, unyielding material. In other embodiments, the engagement portion of plunger rod 14 may include a threaded portion, snap fit mechanism, a ball detent, locking tabs, spring loaded locking mechanism, latch, adhesive, or other similar mechanism. In another alternative embodiment, referring to FIGS. 15A and 15B, the engagement portion of plunger rod 14 may include a plunger rod head 160 having a deformable restraining member such as elastic fingers 162, a stopper contacting portion 164, and a neck 166 disposed between stopper contacting portion 164 and plunger rod head 160. Plunger rod head 160 also includes an annular groove 168 located between elastic fingers 162 and neck 166. Elastic fingers 162 each include a tapered portion 170 and a locking end 172. Plunger rod head 160 will be described in more detail below.

The walls of plunger rod body 64 define an elongate aperture or plunger rod cavity 70. Plunger rod cavity 70 spans the extent of plunger rod body 64 so that plunger rod body 64 is cannulated along its entire length. Plunger rod cavity 70 includes a cavity opening 72, as shown in FIG. 1, adjacent proximal end 62 and terminates at a bottom wall 74 (FIGS. 5A and 5B) adjacent distal end 60. Plunger rod body 64 also defines slots 76 extending between first end 60 and second end 62 of plunger rod 14.

Referring to FIG. 1, in one embodiment, an oxygen absorber 80 can be inserted through cavity opening 72 and into plunger rod cavity 70. Next, a plunger rod cap 82 can be inserted into cavity opening 72 to secure oxygen absorber 80 in plunger rod cavity 70. In one embodiment, plunger rod cap 82 is secured in plunger rod cavity 70 by an interference fit. Referring to FIG. 1, plunger rod cap 82 is sized and adapted to substantially correspond to the interior wall of plunger rod body 64. This interference fit between plunger rod cap 82 and the interior wall of plunger rod body 64 is achieved by sizing and adapting the two mating parts, i.e., the exterior profile of plunger rod cap 82 and the interior profile of the interior wall of plunger rod body 64, so that the exterior profile of plunger rod cap 82 only slightly deviates dimensionally from the interior profile of the interior wall of plunger rod body 64. This ensures an interference fit which secures plunger rod cap 82 within plunger rod cavity 70 by a friction force after insertion of plunger rod cap 82 into plunger rod cavity 70. In alternative embodiments, plunger rod cap 82 can be secured in plunger rod cavity 70 using a taper lock connection or similar connection mechanisms.

By securing oxygen absorber 80 in plunger rod cavity 70, oxygen absorber 80 can reduce the oxygen levels within packaging member 18. Any oxygen contained within packaging member 18 will flow through slots 76 of plunger rod body 64 and will be absorbed by oxygen absorber 80. Typical oxygen absorbing materials that can be used to form oxygen absorber 80 include iron, low molecular weight organic compounds such as ascorbic acid and sodium ascorbate, and polymeric materials incorporating a resin and a catalyst. Reduction of oxygen levels within packaging member 18 is important because atmospheric gases such as oxygen contained in packaging member 18 can cause a medication or drug contained within syringe barrel 12, such as in a pre-filled syringe as discussed above, to degrade. Sealing member 66 of plunger rod 14 provides an additional mechanism to reduce oxygen levels within packaging member 18 by sealing syringe barrel 12 and plunger rod 14 within packaging member 18 as will be described in more detail below.

Referring to FIGS. 1, 2A, and 2B, syringe assembly 10 further includes packaging member 18 which is sized to receive both syringe barrel 12 and plunger rod 14 therein. Packaging member 18 generally includes a first or top end 90, a second or bottom end 92, and a sidewall 94 extending between top end 90 and bottom end 92. Sidewall 94 defines a first compartment 96 and a second compartment 98 of packaging member 18. First compartment 96 is sized and adapted to receive syringe barrel 12 therein and second compartment 98 is sized and adapted to receive plunger rod 14 therein.

Figures 3B, 3C:
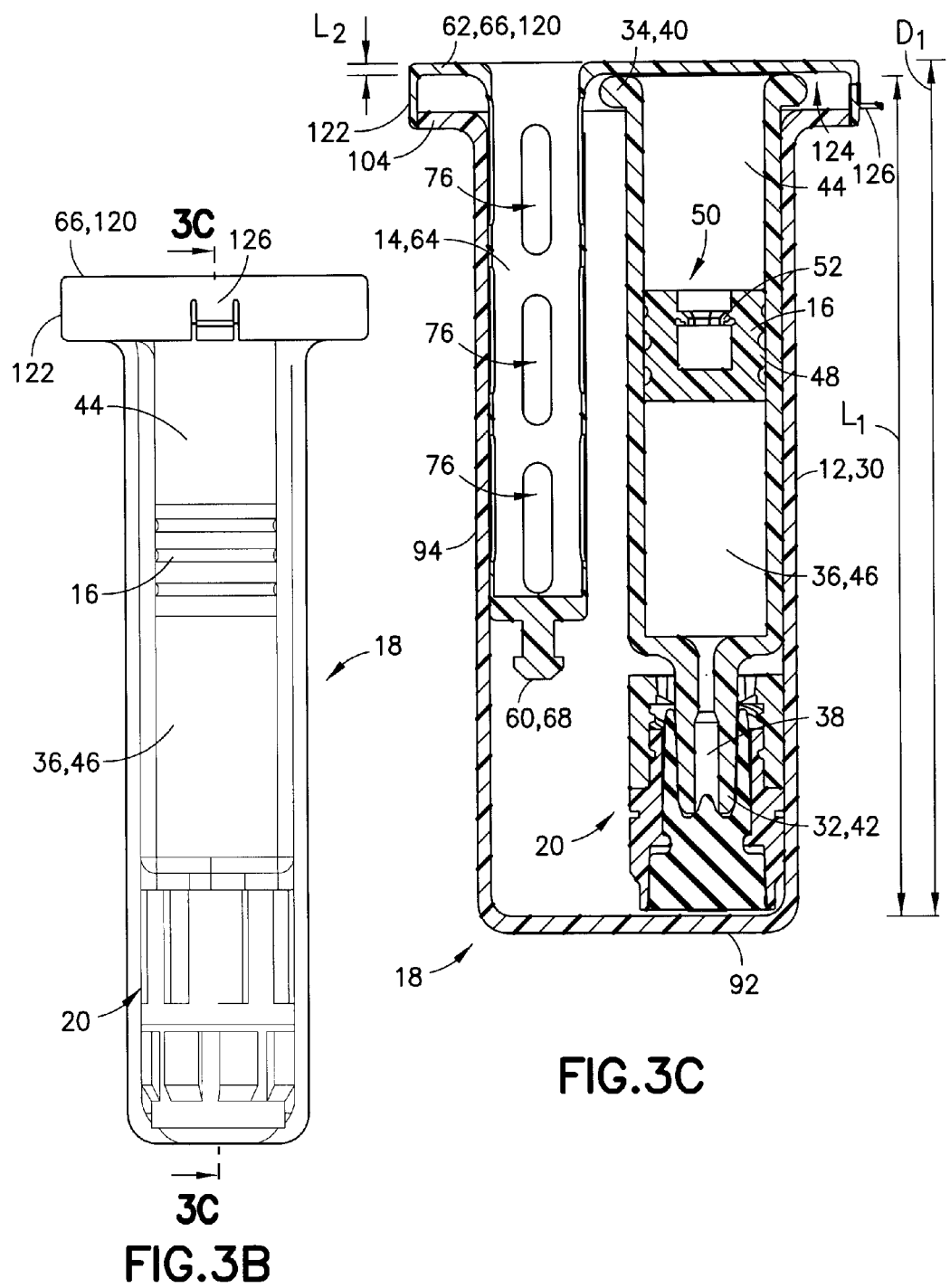
FIG. 3B is a side elevation view of the syringe assembly of FIG. 3A, with a syringe barrel and a plunger rod placed in a packaging member, and a sealing member of the plunger rod sealing the syringe barrel and the plunger rod within the packaging member in accordance with an embodiment of the present invention.
FIG. 3C is a cross-sectional view taken along line 3C-3C of FIG. 3B in accordance with an embodiment of the present invention.

Referring to FIG. 8B, in one embodiment, first compartment 96 has diameter $d_1$ and second compartment 98 has diameter $d_2$. Referring to FIGS. 1 and 3C, in one embodiment, syringe barrel 12 has a larger diameter than the diameter of plunger rod 14. Accordingly, referring to FIG. 8B, diameter $d_1$ of first compartment 96 is greater than diameter $d_2$ of second compartment 98. In this manner, first compartment 96 accommodates syringe barrel 12 and second compartment 98 accommodates plunger rod 14. Referring to FIG. 8B, in one embodiment, the sidewall 94, as shown in FIG. 8A, of packaging member 18 includes opposing protruding portions 100 which together define a connecting channel 102. The distance between opposing protruding portions 100 is less than the diameters $d_1$ and $d_2$ of first compartment 96 and second compartment 98, respectively, and connecting channel 102 is disposed between first compartment 96 and second compartment 98. In this manner, first compartment 96 and second compartment 98 can be formed in a single step manufacturing process such as stamping, punching, or similar process. In some embodiments, first compartment 96 and second compartment 98 can be formed as a unitary embodiment.

Figure 9A:
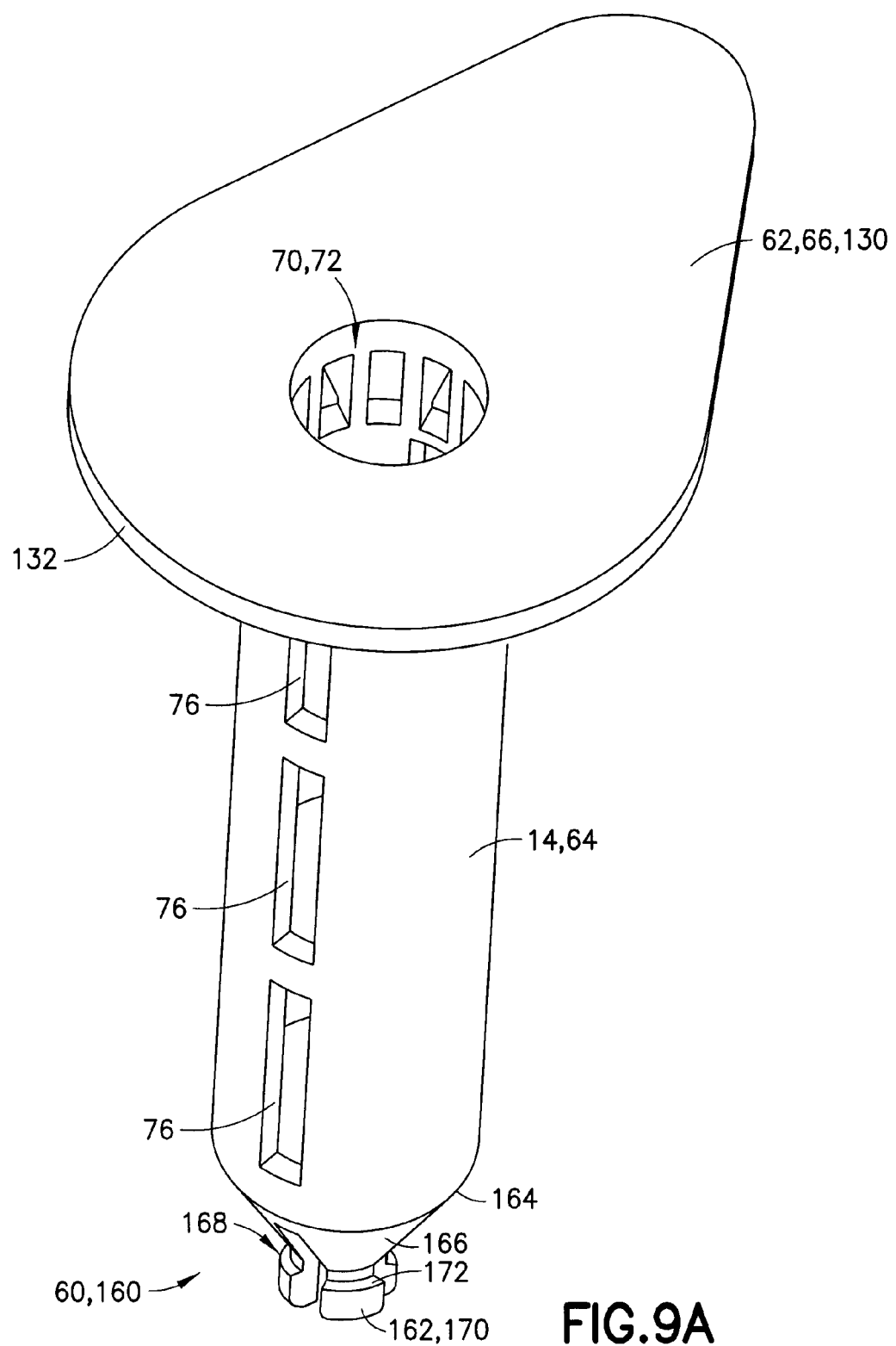
FIG. 9A is a perspective view of the plunger rod of FIG. 7 in accordance with an embodiment of the present invention.
Figure 9B:
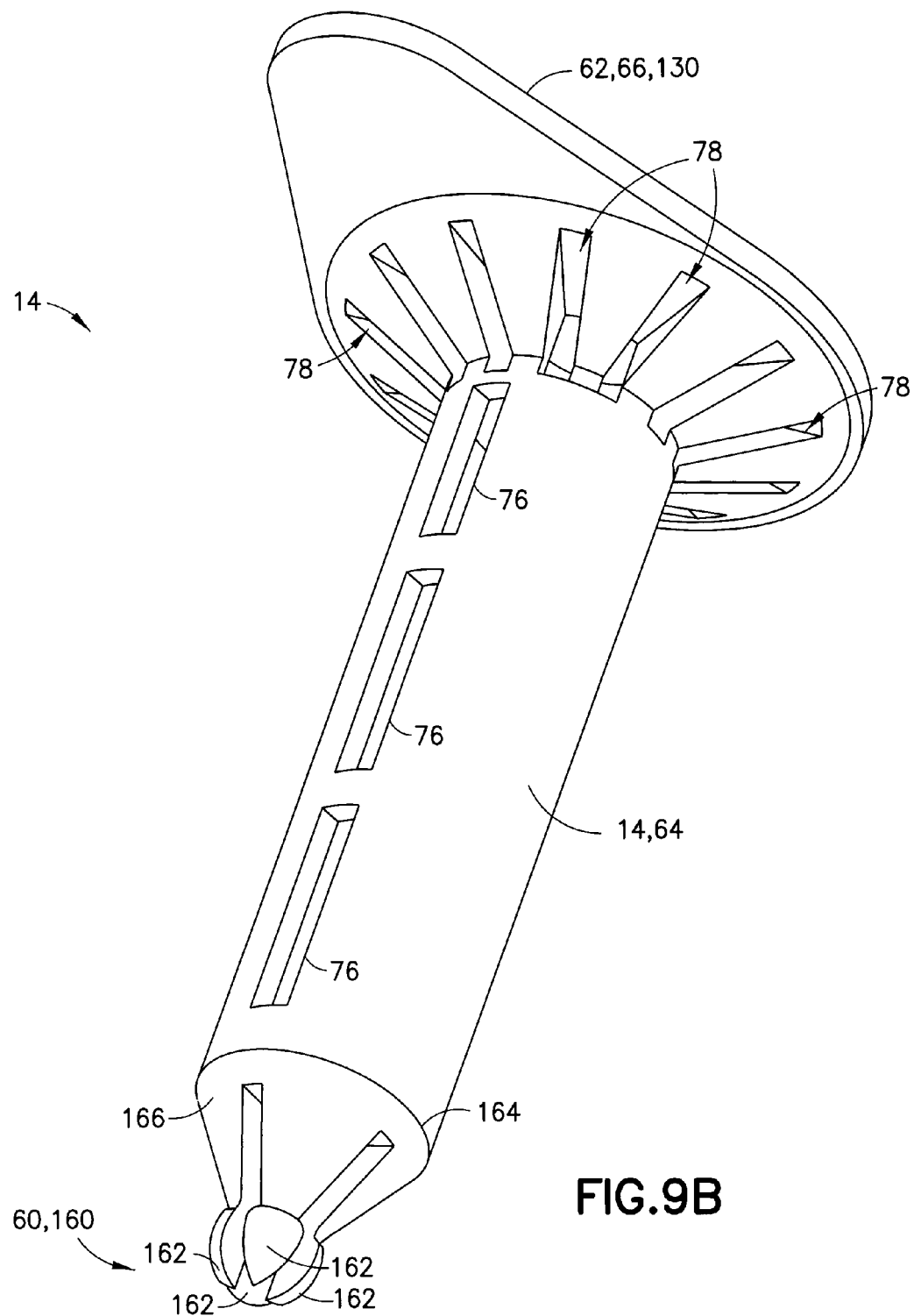
FIG. 9B is a perspective view of the plunger rod of FIG. 9A in accordance with an embodiment of the present invention.
Figure 10:
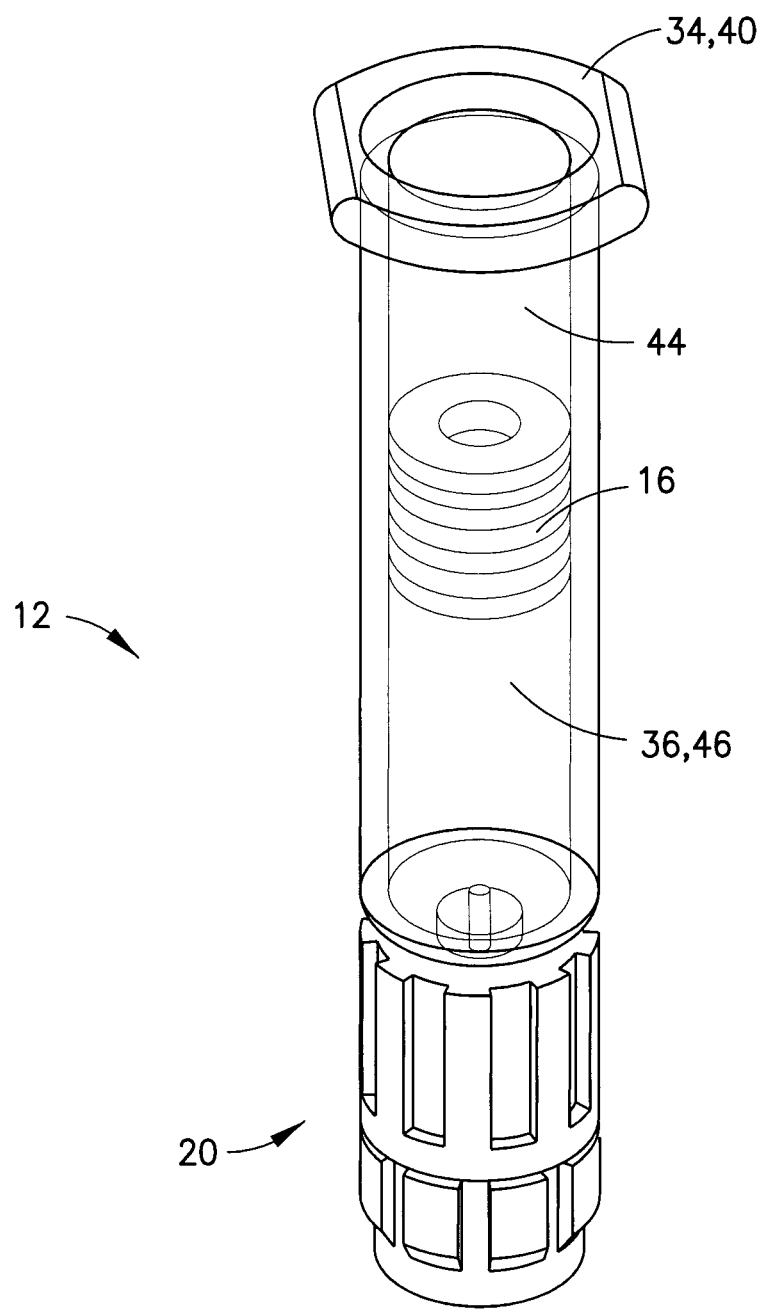
FIG. 10 is a perspective view of the syringe assembly of FIG. 7 in accordance with an embodiment of the present invention.
Figure 11:
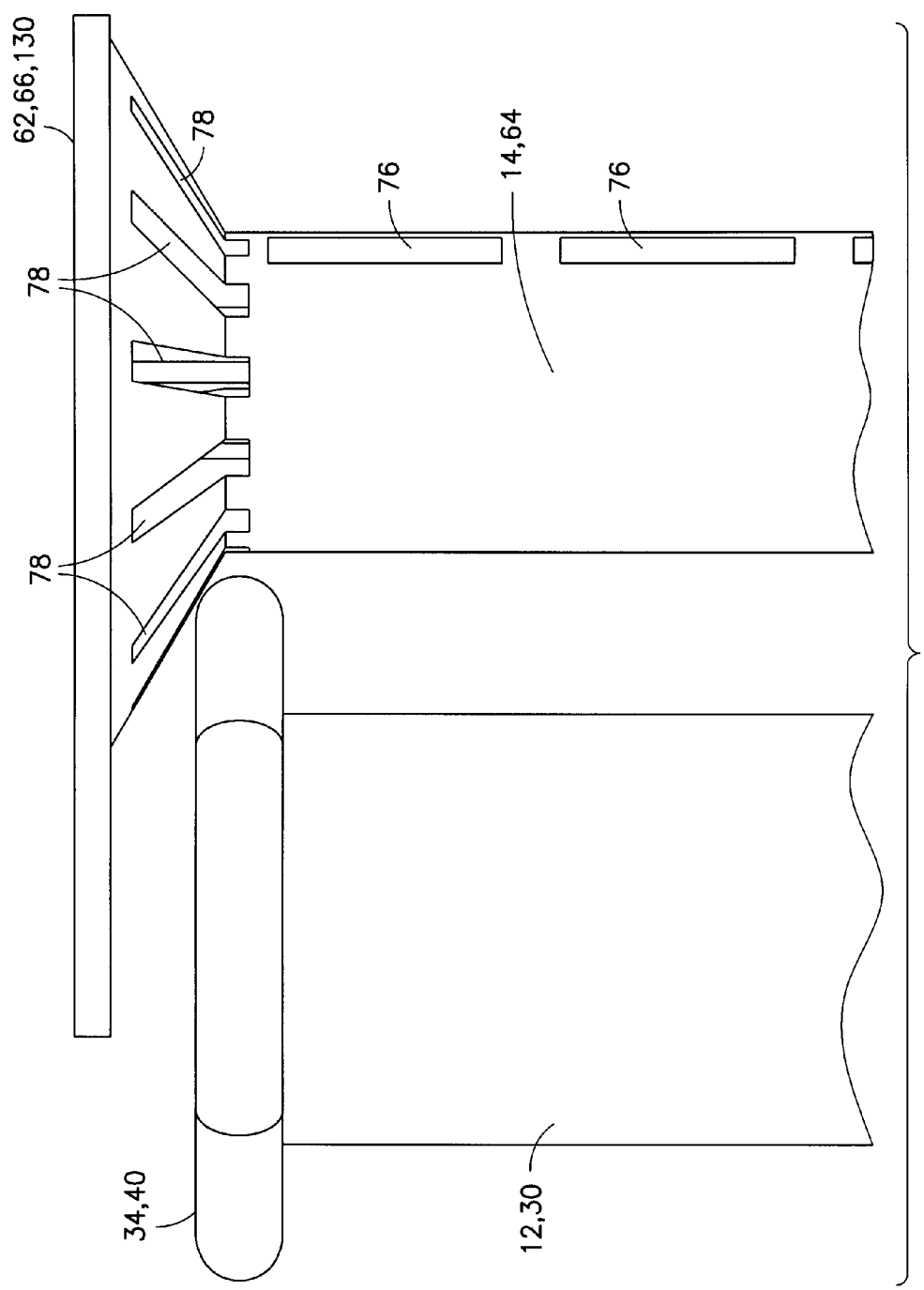
FIG. 11 is a partial elevation view of a top portion of the plunger rod of FIG. 9A and a top portion of the syringe assembly of FIG. 10 in accordance with an embodiment of the present invention.
Figure 12A:
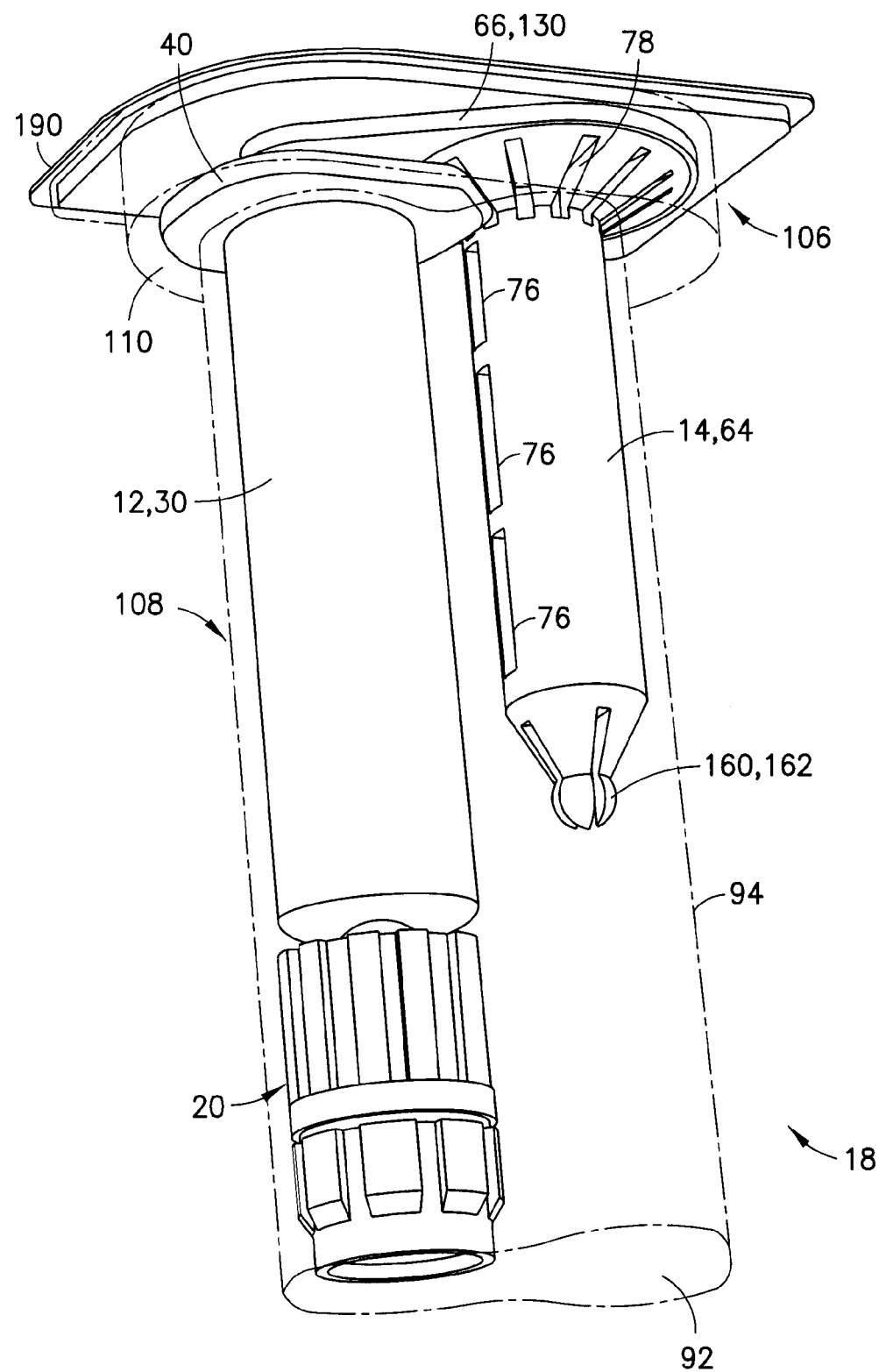
FIG. 12A is a perspective view of the syringe assembly of FIG. 7, with the syringe barrel of FIG. 10 and the plunger rod of FIG. 9A placed in the packaging member of FIG. 8A, and an additional sealing cover disposed over the syringe barrel and the plunger rod within the packaging member in accordance with an embodiment of the present invention.
Figure 12B:
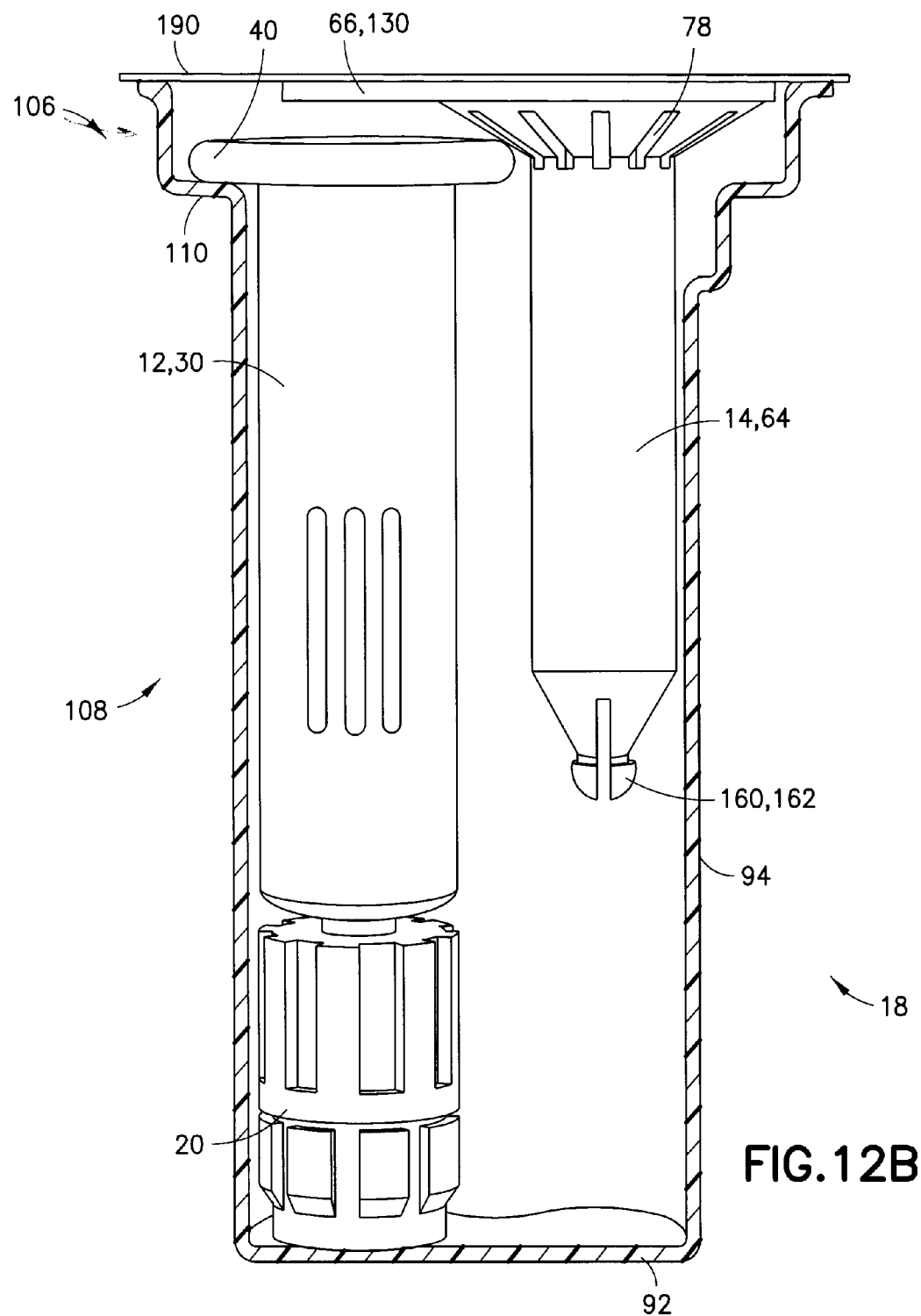
FIG. 12B is a side elevation view of the syringe assembly of FIG. 12A in accordance with an embodiment of the present invention.
Figure 12C:
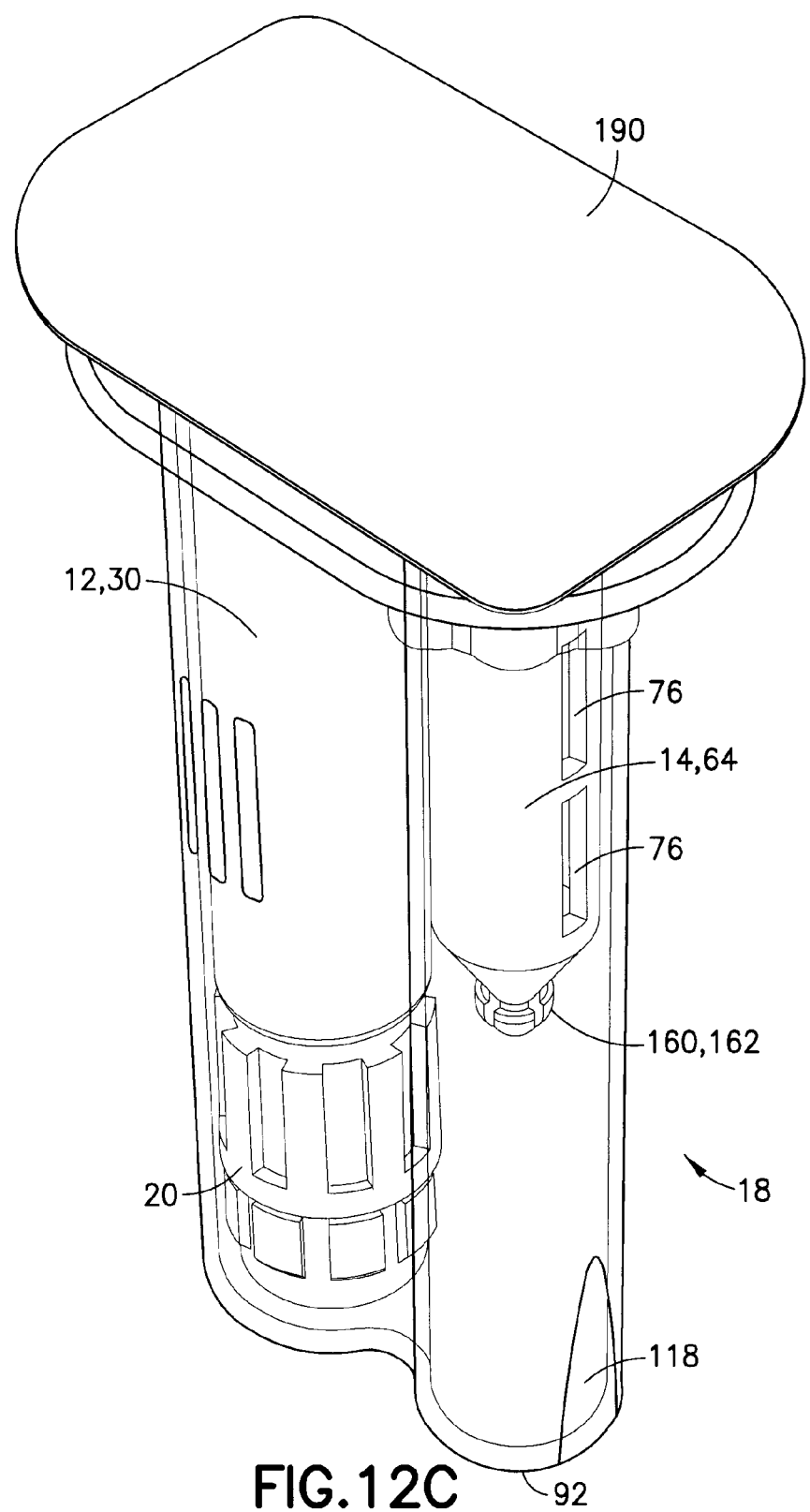
FIG. 12C is a perspective view of the syringe assembly of FIG. 12A in accordance with an embodiment of the present invention.
Figure 12D:
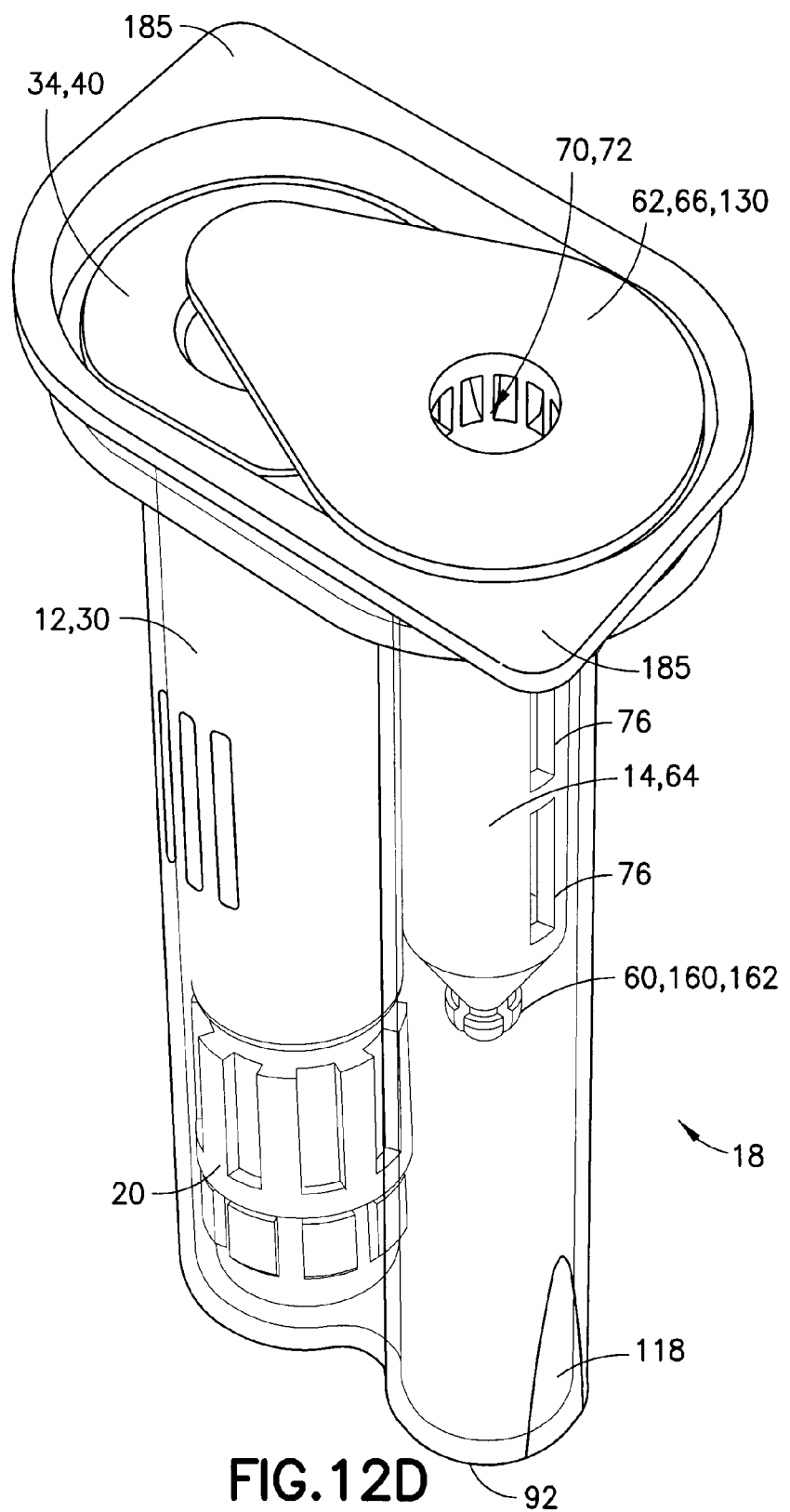
FIG. 12D is a perspective view of the syringe assembly of FIG. 12A, with the additional sealing cover removed in accordance with an embodiment of the present invention.
Figure 13:
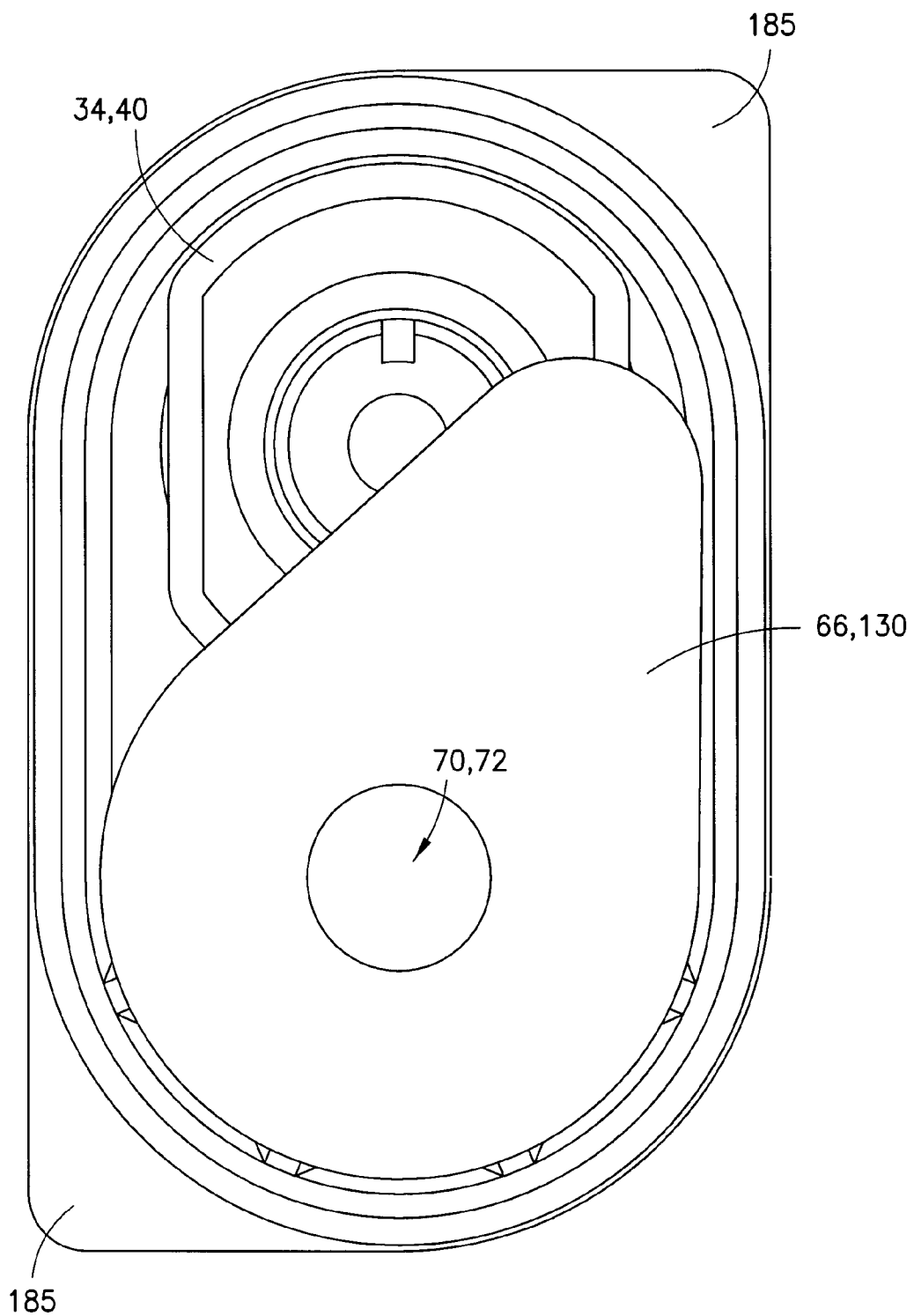
FIG. 13 is a plan view of the syringe assembly of FIG. 12D in accordance with an embodiment of the present invention.
Figure 16A:
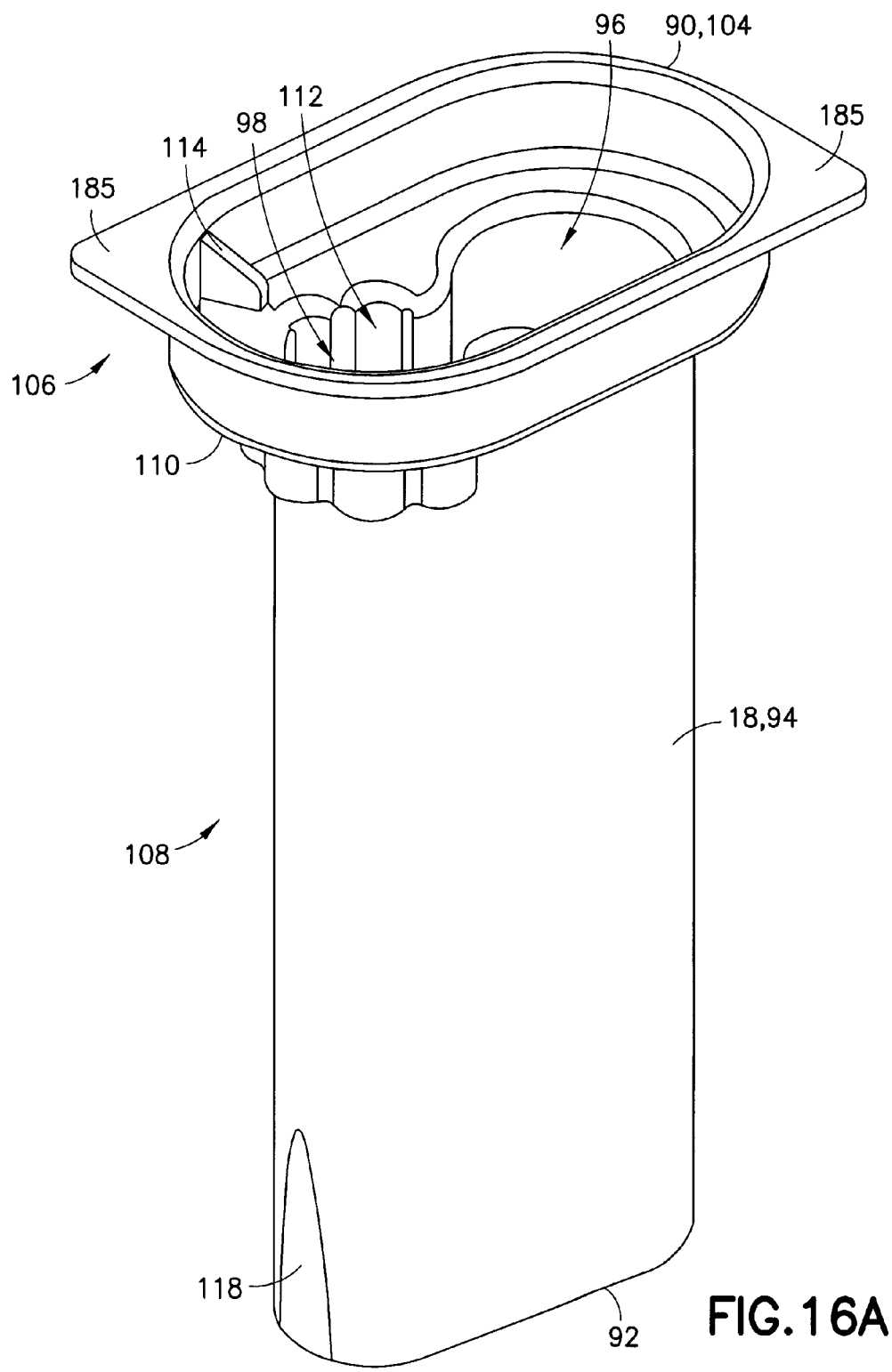
FIG. 16A is a perspective view of a packaging member in accordance with an embodiment of the present invention.

Referring to FIG. 1, packaging member 18 includes a locking lip 104 at top end 90. Disposed below locking lip 104 is an upper tray portion 106 having a cross-section that has a greater area than a cross-section disposed below upper tray portion 106, i.e., a compartment portion 108, such that a shoulder 110 is defined therebetween. Upper tray portion 106 receives and supports flange 40 of syringe barrel 12 and sealing member 66 of plunger rod 14 as will be described in more detail below. Referring to FIG. 8A, in one embodiment, upper tray portion 106 includes vent channels 112 around a periphery of second compartment 98. Vent channels 112 channel and allow any oxygen contained within packaging member 18 to flow through vent channels 112 and slots 76 of plunger rod body 64 so that any oxygen contained within packaging member 18 will be absorbed by oxygen absorber 80 and prevent contamination of medication contained within syringe barrel 12 as discussed above. Referring to FIG. 8A, in one embodiment, upper tray portion 106 includes projection keys 114. Projection keys 114 provide a further securement mechanism to secure plunger rod 14 within second compartment 98 of packaging member 18. For example, referring to FIG. 9B, in one embodiment, the underside surface of flange 66 of plunger rod 14 includes key slots 78. During insertion of plunger rod 14 into packaging member 18, key slots 78 are positioned relative to projection keys 114 and as plunger rod 14 is inserted into second compartment 98, projection keys 114 engage key slots 78, i.e., projection keys 114 are located within key slots 78 of plunger rod 14 and secure plunger rod 14 within packaging member 18. Packaging member 18 may include a number of different features to accommodate a variety of different syringe barrels and plunger rods. For example, referring to FIGS. 8A, 16A, and 16B, packaging member 18 may include elongated depressions 116 and a chamfered end 118 to accommodate syringe barrels and plunger rods having different geometries and/or configurations.

All of the components of syringe assembly 10 may be constructed of any known material, and are desirably constructed of medical-grade polymers.

Referring to FIGS. 1-3C and 12A-12D, packaging of syringe barrel 12 and plunger rod 14 within packaging member 18 will now be described. Initially, syringe barrel 12, plunger rod 14, and packaging member 18 are sterilized according to techniques known to those of ordinary skill in the art. In some embodiments, syringe barrel 12 may be pre-filled as described above. Next, syringe barrel 12 is inserted into first compartment 96 of packaging member 18 such that flange 40 of syringe barrel 12 abuts upper tray portion 106 as shown in FIG. 2B. With syringe barrel 12 properly inserted into first compartment 96 of packaging member 18, plunger rod 14 is then inserted into second compartment 98 of packaging member 18.

Figure 17:
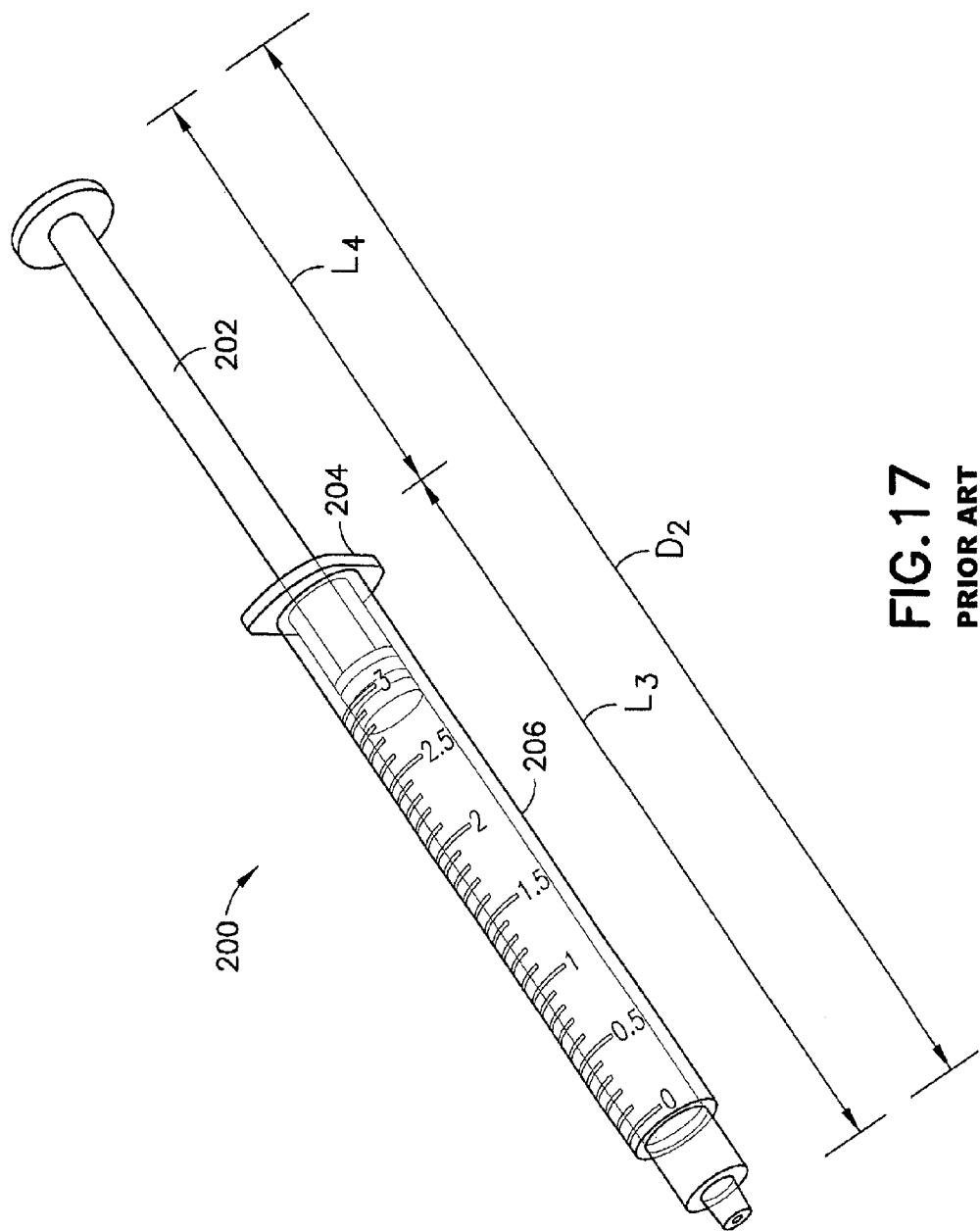
FIG. 17 is a perspective view of a conventional pre-filled syringe in a position to be packaged in accordance with an embodiment of the present invention.

By having syringe assembly 10 including plunger rod 14 separate and detached from syringe barrel 12, plunger rod 14 and syringe barrel 12 can be separately placed in packaging member 18 in a manner that allows for reduced storage space of syringe assembly 10. For example, referring to FIG. 3C, the overall length of syringe assembly 10 in packaging member 18 in a disassembled state, i.e., with plunger rod 14 separate and detached from syringe barrel 12 as shown in FIG. 3C, is equal to the length of syringe barrel 12, i.e., $L_1$, and the thickness of sealing member 66 of plunger rod 14, i.e., $L_2$. As shown in FIG. 3C, in the disassembled state plunger rod 14 and syringe barrel 12 have a first effective distance $D_1$ relative to packaging member 18, i.e., $L_1$ and $L_2$. FIG. 17 illustrates a conventional pre-filled syringe in a position to be packaged. Such a conventional pre-filled syringe, i.e., a syringe assembly 200, is typically packaged with a plunger rod 202 retracted out of a back or proximal end 204 of a syringe barrel 206, with the fluid pre-filled within syringe barrel 206. Accordingly, packaging of such pre-filled syringes is bulky and awkward for shipping and storage. For example, the overall length of pre-filled syringe assembly 200 in the position to be packaged shown in FIG. 17, is equal to the length of syringe barrel 206, i.e., $L_3$, and the length that plunger rod 202 extends outwardly from syringe barrel 206, i.e., $L_4$. As shown in FIG. 17, plunger rod 202 and syringe barrel 206 have a second effective distance $D_2$, i.e., $L_3$ and $L_4$, which is greater than the first effective distance $D_1$ (FIG. 3C) of a syringe assembly in accordance with the present invention. Accordingly, a syringe assembly in accordance with the present invention allows plunger rod 14 and syringe barrel 12 to be packaged in a manner that allows for reduced storage space.

Figure 14:
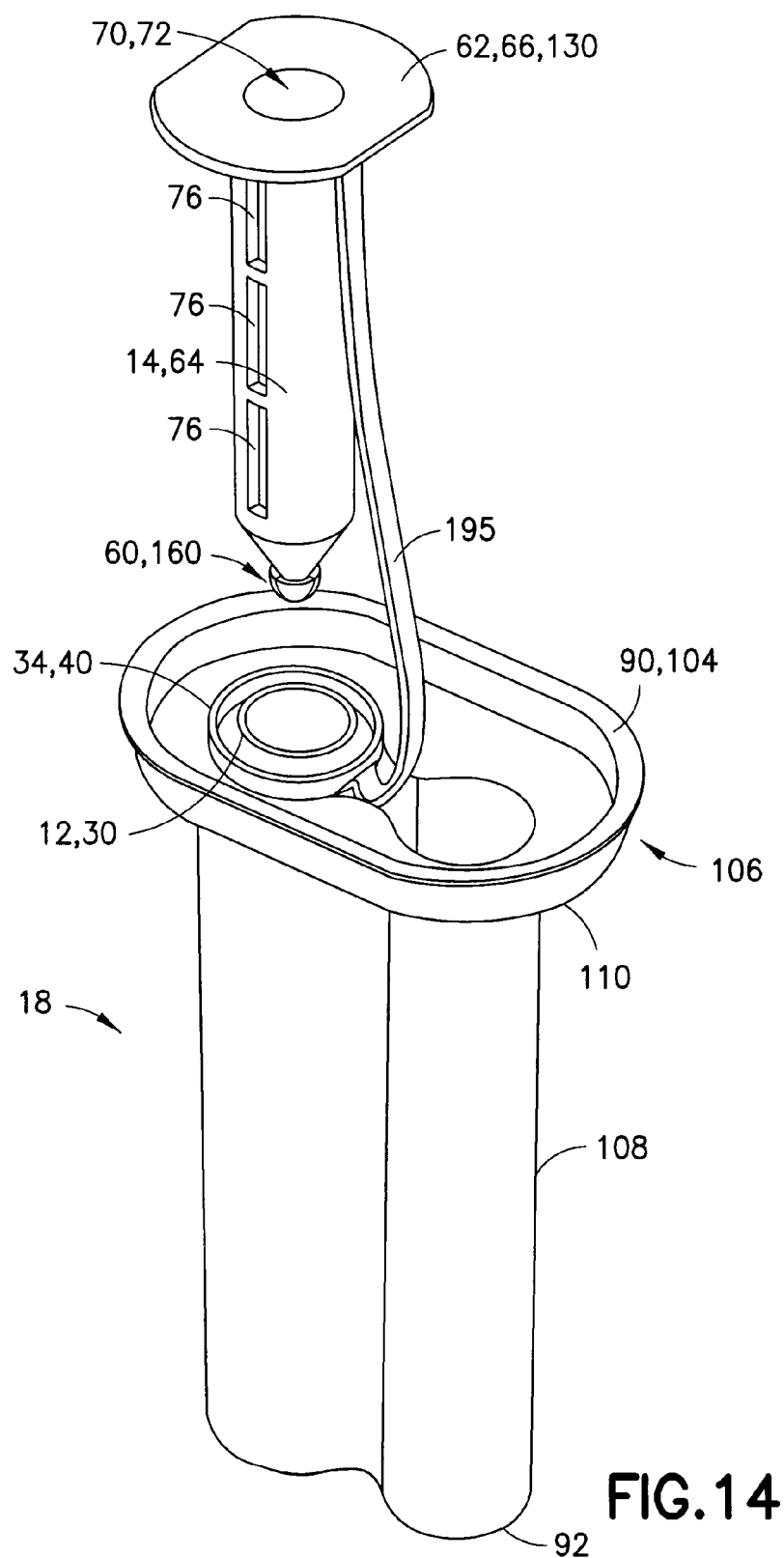
FIG. 14 is a perspective view of a syringe assembly with a tethering member connecting the plunger rod and the syringe barrel in accordance with an embodiment of the present invention.

In an alternative embodiment, referring to FIG. 14, plunger rod 14 and syringe barrel 12 can be separate and detached, but also include a tethering element 195 fastened between plunger rod 14 and syringe barrel 12 to limit the range of movement between the two components.

Additionally, in accordance with a syringe assembly of the present invention, upon removal of plunger rod 14 and syringe barrel 12 from packaging member 18, plunger rod 14 can quickly and easily be secured to syringe barrel 12 for collecting a fluid and/or delivering a fluid as will be described in more detail below.

As described above, referring to FIGS. 3B and 3C, with syringe barrel 12 properly inserted into first compartment 96 of packaging member 18, plunger rod 14 is inserted into second compartment 98 of packaging member 18 such that sealing member 66 of plunger rod 14 seals syringe barrel 12 and plunger rod 14 within packaging member 18, i.e., sealing member 66 of plunger rod 14 provides a substantially impermeable enclosure with respect to packaging member 18, provides a leak prevention and protection enclosure, protects the contents of syringe assembly 10 contained within packaging member 18, and/or maintains a sealed, sterilized environment within packaging member 18. Sealing member 66 of plunger rod 14 provides a sufficient seal at a range of temperatures, pressures, and humidity levels.

Referring to FIGS. 2A, 2B, 3B, and 3C, an embodiment of sealing member 66 of plunger rod 14 is illustrated. In such an embodiment, sealing member 66 comprises a cap member 120 generally including a sidewall 122 extending around its periphery and defining a recessed portion 124, and a locking portion 126. In this embodiment, with syringe barrel 12 properly inserted into first compartment 96 of packaging member 18, plunger rod 14 is then inserted into second compartment 98 of packaging member 18 such that cap member 120 seals syringe barrel 12 and plunger rod 14 within packaging member 18. This is achieved by engagement between sidewall 122 with locking lip 104 of packaging member 18. In one embodiment, cap member 120 can snap over locking lip 104 of packaging member 18 such that locking lip 104 of packaging member 18 is received within recessed portion 124 of cap member 120, and sidewall 122 of cap member 120 engages over locking lip 104 to seal cap member 120 to packaging member 18. In some embodiments, the interior surface of sidewall 122 of cap member 120 can include an annular groove around its inner periphery so that as cap member 120 snaps over locking lip 104, locking lip 104 can be received into the annular groove along the interior surface of sidewall 122 to further secure and seal cap member 120 to packaging member 18. In another embodiment, sidewall 122 can include an interior threaded portion and locking lip 104 of packaging member 18 can include an exterior threaded portion, and cap member 120 can be threadingly connected to locking lip 104 of packaging member 18. In some embodiments, locking portion 126 is formed of a resilient material and can be compressed as cap member 120 is secured to locking lip 104 of packaging member 18 such that once cap member 120 engages locking lip 104, locking portion 126 can spring back to its original form or position and engage an aperture disposed within a portion of locking lip 104 of packaging member 18 to further secure and seal cap member 120 to packaging member 18. In other embodiments, cap member 120 and packaging member 18 can also include mating locking tabs, a ball detent mechanism, a spring loaded locking mechanism, latch, adhesive, or other similar mechanism to further secure and seal cap member 120 to packaging member 18. In one embodiment, tamper evidence is also provided by use of a tear strip or other indicating means secured to a portion of cap member 120 and packaging member 18 to indicate tampering with the contents of packaging member 18.

Referring to FIGS. 1, 3A, 4, 6A, and 6B, an embodiment of sealing member 66 of plunger rod 14 is illustrated. In such an embodiment, sealing member 66 comprises a sealing flange 130 generally including a sidewall 132 having a constant thickness. In this embodiment, locking lip 104 of packaging member 18 can include an annular groove on its interior surface for receiving a sealing mechanism such as an o-ring around sidewall 132 of sealing flange 130 to secure sealing flange 130 to packaging member 18. Sealing flange 130 can be formed of a resilient material sized relative to the profile of locking lip 104 of packaging member 18 so that as sealing flange 130 is forced in locking lip 104, locking lip 104 compresses sealing flange 130 until sealing flange 130 reaches the annular groove on the interior surface of locking lip 104. At this position, sealing flange 130 returns to its original position and locks inside of the annular groove on the interior surface of locking lip 104. In other embodiments, referring to FIGS. 12A-12C, an additional sealing cover 190 can be secured over sealing flange 130 and packaging member 18 to provide an additional seal mechanism. In one embodiment, tamper evidence is also provided by use of a tear strip or other indicating means secured to a portion of sealing flange 130 and packaging member 18 to indicate tampering with the contents of packaging member 18.

Referring to FIGS. 8A and 8B, packaging member 18 can also include opposing flanges 185 located at top end 90. In such an embodiment, sealing flange 130 of plunger rod 14 can have a shape that corresponds to the profile of top end 90 of packaging member 18 with opposing flanges 185. In this manner, in one embodiment, sealing flange 130 can be secured to opposing flanges 185 of packaging member 18 by an adhesive connection between the exterior surface of opposing flanges 185 and the underside surface of sealing flange 130 of plunger rod 14. In another embodiment, referring to FIGS. 12A-12C, additional sealing cover 190 can be secured to packaging member 18 in a similar way using such an adhesive connection.

Referring to FIGS. 1, 3B, 3C, 4, and 6B, removal of syringe barrel 12 and plunger rod 14 from packaging member 18 so that syringe barrel 12 and plunger rod 14 can be secured together to form a syringe assembly to expel a fluid, such as a medication, contained within distal chamber 46 of syringe barrel 12 will now be described. Initially, the user removes syringe assembly 10 from packaging member 18. To remove syringe assembly 10 from packaging member 18, in one embodiment, a user can first check to make sure a tear strip or other tamper evidence member has not been broken. Next, the user can remove the tamper evidence member and then break the above described seal between sealing member 66 of plunger rod 14 and packaging member 18.

With the seal between sealing member 66 of plunger rod 14 and packaging member 18 broken, a user can grasp sealing member 66 and pull sealing member 66 longitudinally to remove plunger rod 14 from second compartment 98 of packaging member 18. Next, a user can grasp flange 40 located in upper tray portion 106 of packaging member 18 and pull flange 40 longitudinally to remove syringe barrel 12 from first compartment 96 of packaging member 18. With plunger rod 14 and syringe barrel 12 removed from packaging member 18, plunger rod 14 and syringe barrel 12 can be secured together to form syringe assembly 10 adapted for dispensing and delivery of a fluid and/or collection of a fluid.

Referring to FIGS. 4-6B, an embodiment of a securement feature operable to secure plunger rod 14 to syringe barrel 12 via stopper 16 will now be described. With plunger rod head 68 of plunger rod 14 positioned adjacent plunger receiving aperture 50 of stopper 16, plunger rod 14 is inserted or moved axially into plunger receiving aperture 50 in a direction generally along arrow A (FIG. 5A), such that tapered portion 148 of plunger rod head 68 is disposed within plunger receiving aperture 50 of stopper 16. As additional force is exerted on plunger rod 14 to axially move plunger rod head 68 in the direction generally along arrow A within plunger receiving aperture 50, tapered portion 148 of plunger rod head 68 cooperates with tapered portion 54 of a deformable restraining member, such as elastic fingers 52, and deforms or compresses elastic fingers 52 of stopper 16 outward in a direction generally along arrow C (FIG. 5A) until plunger rod head 68 advances beyond, i.e., slides over and past, elastic fingers 52 and locks plunger rod 14 to stopper 16 as shown in FIG. 5B. Once plunger rod head 68 slides over and past elastic fingers 52, elastic fingers 52 of stopper 16 return to their undeformed or original position as shown in FIGS. 5A and 5B. In this position, referring to FIG. 5B, locking end 56 of elastic fingers 52 abut, contact, or engage shoulder wall 144 of plunger rod head 68 and lock or secure plunger rod 14 to stopper 16. This configuration ensures that with elastic fingers 52 mechanically locked over shoulder wall 144 of plunger rod head 68, plunger rod 14 is secured to stopper 16, such that, significant relative movement between plunger rod 14 and stopper 16 is prevented. In this manner, plunger rod 14 is adapted for advancing stopper 16 within syringe barrel 12. In a further configuration, the stopper 16 may include an insert adapted for engagement with the plunger rod 14. The insert may be formed of a different material than the material used to form the stopper 16. In this fashion, different material properties would be permitted for the portion of the stopper 16 that seals against the syringe barrel 30 as compared to the material properties of the of the portion of the stopper that engages the plunger rod 14.

Figure 15A:
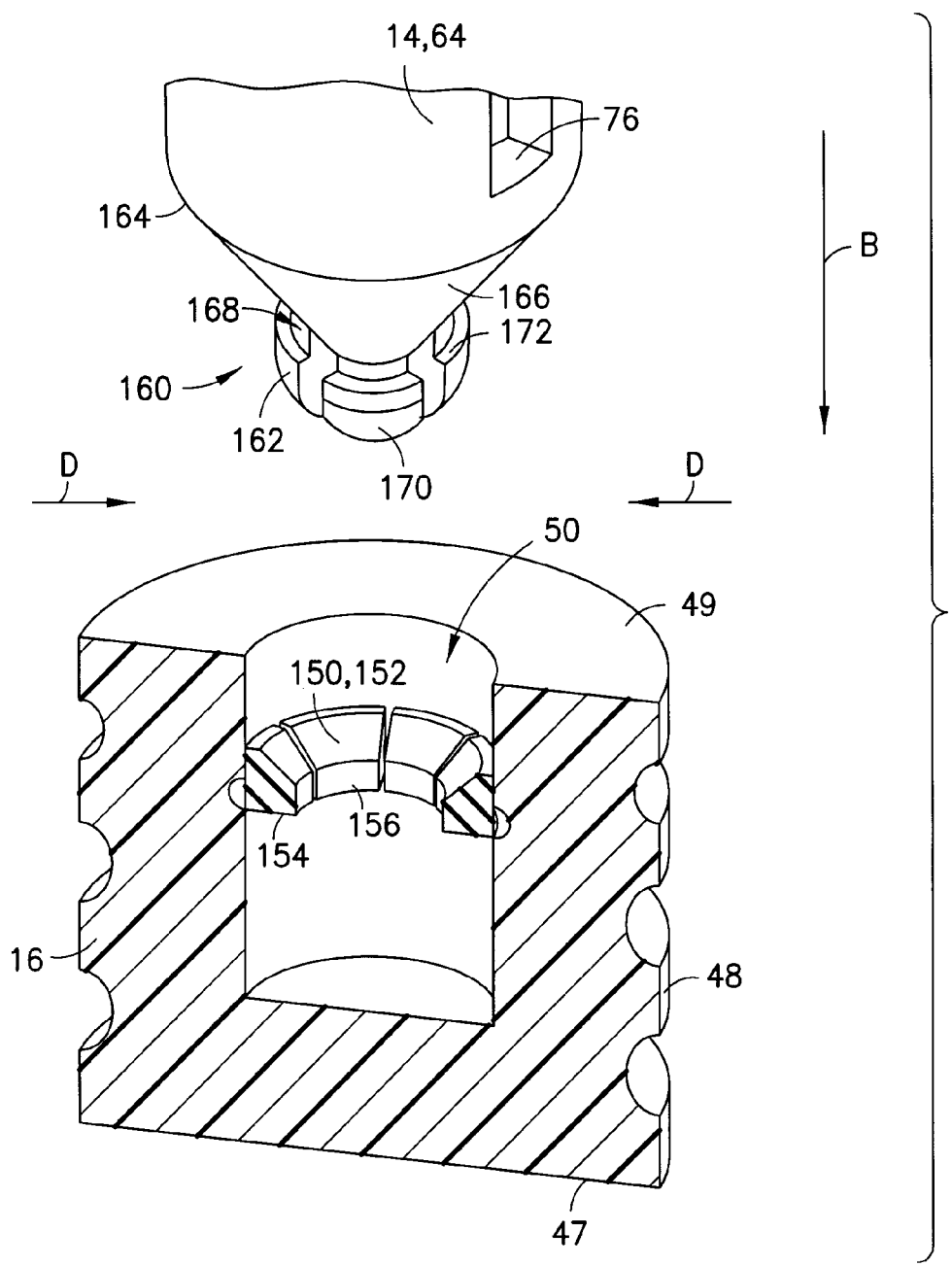
FIG. 15A is a fragmentary, cross-sectional view of a securement feature of the syringe barrel and the plunger rod in a disengaged position in accordance with an embodiment of the present invention.
Figure 15B:
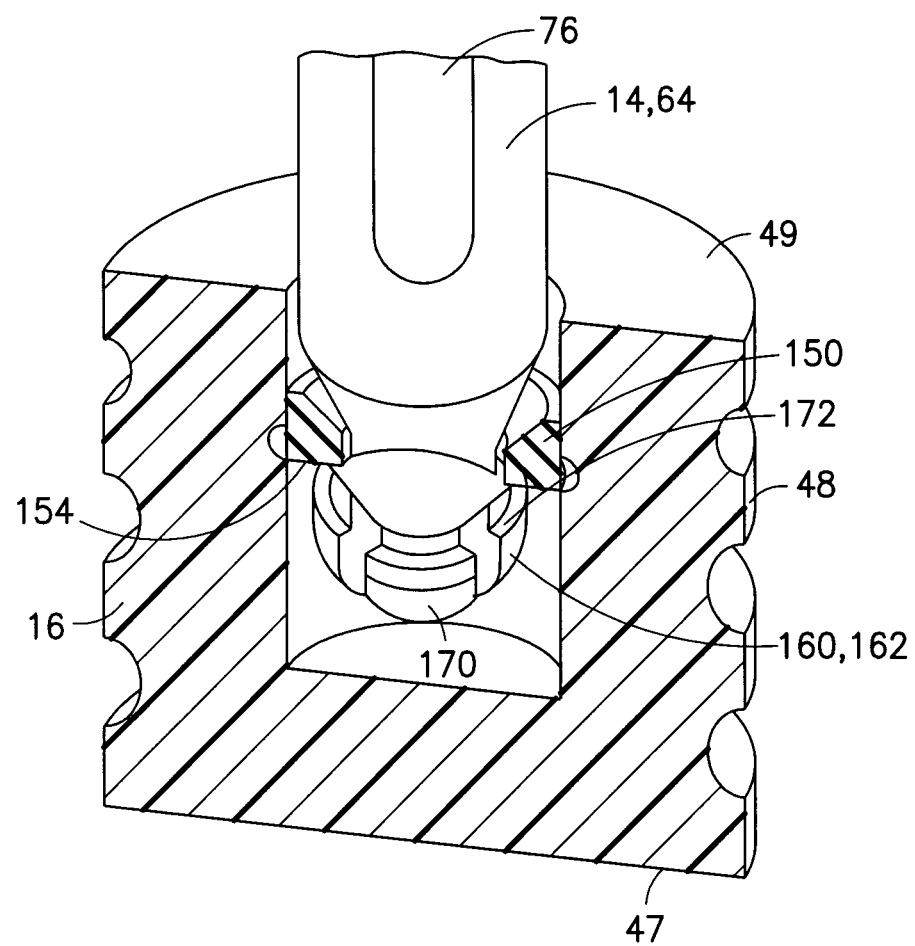
FIG. 15B is a fragmentary, cross-sectional view of the securement feature of FIG. 15A in an engaged position in accordance with an embodiment of the present invention.

Referring to FIGS. 15A and 15B, another exemplary embodiment of a securement feature operable to secure plunger rod 14 to stopper 16 will now be described. With plunger rod head 160 of plunger rod 14 positioned adjacent plunger receiving aperture 50 of stopper 16, plunger rod 14 is inserted or moved axially into plunger receiving aperture 50 in a direction generally along arrow B (FIG. 15A), such that elastic fingers 162 of plunger rod head 160 is disposed within plunger receiving aperture 50 of stopper 16. As additional force is exerted on plunger rod 14 to axially move plunger rod head 160 in the direction generally along arrow B within plunger receiving aperture 50, tapered portion 170 of elastic fingers 162 cooperates with tapered portion 152 of protruding member 150 and protruding member 150 pushes or compresses elastic fingers 162 of plunger rod head 160 inward in a direction generally along arrow D (FIG. 15A) until elastic fingers 162 of plunger rod head 160 slide over and past tapered portion 152 of protruding member 150 and lock plunger rod 14 to stopper 16 as shown in FIG. 15B. Once elastic fingers 162 of plunger rod head 160 slide over and past tapered portion 152 of protruding member 150, elastic fingers 162 return to their original position as shown in FIGS. 15A and 15B. In this position, referring to FIG. 15B, locking end 154 of protruding member 150 abuts, contacts, or engages locking end 172 of elastic fingers 162 with protrusion 156 of protruding member 150 disposed adjacent annular groove 168 of plunger rod head 160 and locks or secures plunger rod 14 to stopper 16. This configuration ensures that with elastic fingers 162 mechanically locked over protruding member 150, plunger rod 14 is secured to stopper 16, such that significant relative movement between plunger rod 14 and stopper 16 is prevented. In this manner, plunger rod 14 is adapted for advancing stopper 16 within syringe barrel 12.

In an alternative embodiment, plunger rod 14 can be secured to syringe barrel 12 via stopper 16 by threadingly engaging a threaded portion of plunger rod 14 to a threaded portion of stopper 16. In other embodiments, plunger rod 14 can be secured to stopper 16 using a ball detent, locking tabs, spring loaded locking mechanism, latch, adhesive, or other similar mechanism. In all embodiments, plunger rod 14 is locked, secured, or engaged to stopper 16, i.e., significant relative movement between plunger rod 14 and stopper 16 is prevented and movement of plunger rod 14 can be transferred to stopper 16 to slide stopper 16 between positions within syringe barrel 12. In other alternate embodiments, plunger rod 14 and stopper 16 may be integrally formed and both form a plunger assembly positioned within second compartment 98 of packaging member 18 and separate syringe barrel 12 positioned within first compartment 96 of packaging member 18.

In other embodiments, plunger rod 14 and stopper 16 may be co-formed such as by co-extrusion. In alternate embodiments, plunger rod 14 and stopper 16 may be integrally formed as a plunger assembly that is securable to syringe barrel 12. In an alternative embodiment, stopper 16 may include a stopper adapter co-formed therewith and plunger rod 14 engageable with the stopper adapter.

Next, referring to FIG. 6B, with plunger rod 14 and syringe barrel 12 secured together to form syringe assembly 10, a user can remove sealing cap member 20 from distal end 32 of syringe barrel 12. A user can then attach tip 42 of syringe barrel 12 to a separate needle assembly or IV connection assembly and lockingly engage the needle assembly or IV connection assembly to tip 42 of syringe barrel 12 in a known manner. Prior to dispensing any medication, any air trapped within distal chamber 46 of syringe barrel 12 can be expelled in a known manner.

Referring to FIG. 6B, the use of syringe assembly 10 to expel a fluid, such as a medication, contained within distal chamber 46 of syringe barrel 12 will now be described. Movement of flange 66 of plunger rod 14 provides actuation means for moving or sliding stopper 16 between positions within syringe barrel 12. For example, flange 66 may have any shape that allows a user to grip and actuate flange 66 in a back and forth direction.

When it is desired to expel or deliver the medication contained within syringe barrel 12, syringe assembly 10 is grasped with the user's thumb on flange 66 of plunger rod 14 and with the user's fingers grasping and extending around flange 40 of syringe barrel 12. In this manner, syringe assembly 10 is grasped by a user in a well known and well recognized manner similar to the operation of a conventional hypodermic syringe. Next, the user effects a squeezing movement between the thumb on flange 66 of plunger rod 14 and four fingers grasping flange 40 of syringe barrel 12, thereby causing flange 66 of plunger rod 14 to move in a direction generally along arrow E (FIG. 6B) toward proximal end 34 of syringe barrel 12. In this manner, movement of stopper 16 in the direction generally along arrow E forces the fluid contained within distal chamber 46 of syringe barrel 12 to be forced out outlet opening 38, i.e., movement of stopper 16 towards distal end 32 of syringe barrel 12 reduces the volume of distal chamber 46 and forces the fluid from syringe barrel 12. The fluid can be expelled from syringe barrel 12 through outlet opening 38 for contact with a patient and/or into a separate needle assembly or IV assembly and into the patient.

Referring now to FIG. 6B, the use of syringe assembly 10 to fill syringe barrel 12 with medication from a separate vial prior to use will now be described. With syringe assembly in a position in which stopper 16 is located adjacent distal end 32 of syringe barrel 12 and with a needle assembly locked to distal end 32 of syringe barrel 12 and placed in a vial containing fluid, when it is desired to aspirate or pull the fluid, such as a medication, into distal chamber 46 of syringe barrel 12, a user moves flange 66 of plunger rod 14 in a direction generally along arrow F (FIG. 6B) and away from proximal end 34 of syringe barrel 12 until the desired amount of the fluid is pulled into distal chamber 46 of syringe barrel 12.

In this manner, movement of stopper 16 in the direction generally along arrow F creates a vacuum inside distal chamber 46 of syringe barrel 12. As the user moves stopper 16, via plunger rod 14 in the direction generally along arrow F, the user actively increases the volume within distal chamber 46 of syringe barrel 12. Because the stopper is sized relative to syringe barrel 12 to provide sealing engagement with the interior wall of syringe barrel 12, as describe above, and because the needle assembly locked to distal end 32 of syringe barrel 12 is placed in a vial containing fluid, no air can enter into distal chamber 46 of syringe barrel 12 and, thus, the same number of air molecules are located within distal chamber 46 as the user actively increases the volume within distal chamber 46. This decreases the pressure in distal chamber 46 of syringe barrel 12 relative to the air pressure outside of syringe barrel 12. Therefore, a vacuum, i.e., a space of lower air pressure, is created to pull the fluid, such as a medication, into distal chamber 46 of syringe barrel 12. Advantageously, syringe assembly 10 can be used to collect a fluid into distal chamber 46 of syringe barrel 12 or to expel a fluid out of distal chamber 46 of syringe barrel 12.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A syringe packaging system, comprising:
  a syringe barrel having a first end, a second end, and a sidewall extending therebetween and defining a chamber having an interior;
  a stopper slidably disposed within the interior of the chamber of the syringe barrel;
  a plunger rod having a first end engageable with a portion of the stopper and a sealing member that forms an opposite second end; and
  a packaging member having a first end, a second end, and a sidewall defining a first compartment and a second compartment each extending between the first end and the second end of the packaging member, the syringe barrel receivable within the first compartment, and the plunger rod receivable with the second compartment,
  wherein with the syringe barrel received within the first compartment of the packaging member and the plunger rod received within the second compartment of the packaging member, the sealing member of the plunger rod seals the syringe barrel and the plunger rod within the packaging member,
  wherein the plunger rod comprises a cavity that terminates at the first end and includes an opening in the sealing member adjacent the opposite second end, and wherein an oxygen absorber is contained within the plunger rod cavity within the plunger rod.

2. The syringe packaging system of claim 1, wherein the first compartment and the second compartment are formed as a unitary compartment.

3. The syringe packaging system of claim 1, wherein the stopper comprises a stopper adapter co-formed therewith and the first end of the plunger rod is engageable with the stopper adapter.

4. The syringe packaging system of claim 1, further comprising a medication or drug disposed within the chamber.

5. The syringe packaging system of claim 1, further comprising a tethering element fastened between the syringe barrel and the plunger rod to limit the range of movement between the syringe barrel and the plunger rod.

6. The syringe packaging system of claim 1, wherein the packaging member is substantially rigid.

7. The syringe packaging system of claim 1, wherein the plunger rod comprises slots extending between the first end and the second end such that the oxygen absorber is in fluid communication with the first compartment.

8. A syringe packaging system, comprising:
  a syringe barrel having a first end, a second end, and a sidewall extending therebetween and defining a chamber having an interior;
  a stopper slidably disposed within the interior of the chamber of the syringe barrel;
  a plunger rod having a first end engageable with a portion of the stopper and a sealing member that forms an opposite second end;
  an oxygen absorber contained within the plunger rod; and
  a packaging member having a first end, a second end, and a sidewall defining a first compartment and a second compartment each extending between the first end and the second end of the packaging member, the syringe barrel receivable within the first compartment and the plunger rod receivable within the second compartment, wherein the sealing member of the plunger rod seals the syringe barrel and the plunger rod within the packaging member,
  wherein the plunger rod comprises a cavity that terminates at the first end and includes an opening in the sealing member adjacent the opposite second end, and wherein an oxygen absorber is contained within the plunger rod cavity within the plunger rod.

9. The syringe packaging system of claim 8, wherein the packaging member is substantially rigid.

* * * * *